United States Patent
Chekan et al.

(10) Patent No.: US 8,986,331 B2
(45) Date of Patent: Mar. 24, 2015

(54) INSTRUMENT FOR DEBRIDING FISTULA AND APPLYING THERAPEUTIC CELLS

(75) Inventors: Edward G. Chekan, Cincinnati, OH (US); Kevin L. Houser, Springboro, OH (US); Robert E. Sackett, Maineville, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 310 days.

(21) Appl. No.: 12/778,731

(22) Filed: May 12, 2010

(65) Prior Publication Data

US 2011/0282373 A1    Nov. 17, 2011

(51) Int. Cl.
*A61B 17/22*    (2006.01)
*A61B 17/32*    (2006.01)
*A61M 25/00*    (2006.01)
*A61B 17/00*    (2006.01)
*A61M 25/01*    (2006.01)
*A61B 18/14*    (2006.01)
(Continued)

(52) U.S. Cl.
CPC ....... *A61B 17/0057* (2013.01); *A61B 17/32002* (2013.01); *A61B 2017/00969* (2013.01); *A61B 2017/00641* (2013.01); *A61B 2017/00623* (2013.01); *A61M 25/007* (2013.01); *A61M 2025/0175* (2013.01); *A61B 2217/005* (2013.01); *A61B 18/1492* (2013.01); *A61B 17/00491* (2013.01); *A61B 2017/320004* (2013.01); *A61B 2217/007* (2013.01); *A61B 10/0283* (2013.01); *A61B 2017/00893* (2013.01); *A61M 1/0084* (2013.01); *A61B 2018/1472* (2013.01); *A61B 2017/00654* (2013.01); *A61B 2017/320775* (2013.01); *A61B 2017/00398* (2013.01); *A61B 2017/32006* (2013.01)

USPC ......................................................... 606/159

(58) Field of Classification Search
USPC .............. 604/93.01, 264; 606/167, 170, 184, 606/185, 159
See application file for complete search history.

(56) References Cited

U.S. PATENT DOCUMENTS 5,364,395 A    11/1994    West, Jr.
5,526,822 A    6/1996    Burbank et al.
(Continued)

FOREIGN PATENT DOCUMENTS

GB    2 450 411    12/2008
WO    WO 97/39685    10/1997
(Continued)

OTHER PUBLICATIONS

U.S. Appl. No. 12/483,305, filed Jun. 12, 2009, Hibner et al.
(Continued)

*Primary Examiner* — Ashley Fishback

(57) ABSTRACT

A treatment instrument comprises an end effector and a plunger. The end effector comprises a plurality of cutting features and an interior cavity. At least a portion of the plunger is slidably positioned within the interior cavity of the end effector. The plunger comprises a distal head attached to the distal end of a central shaft. The plunger is configured to rotate within the end effector, and comprises a cutting member that is operable to mince tissue specimens captured by the cutting features of the end effector. An alternative treatment system comprises an end effector, a plunger, and a plug. The central shaft of the plunger and the plug are slidably located within an inner tube of the end effector, with the plug being positioned distal to the central shaft.

18 Claims, 25 Drawing Sheets

(51) Int. Cl.
*A61B 10/02* (2006.01)
*A61M 1/00* (2006.01)
*A61B 17/3207* (2006.01)

(56) References Cited

U.S. PATENT DOCUMENTS

| | | |
|---|---|---|
| 5,694,951 A | 12/1997 | Bonutti |
| 6,066,153 A | 5/2000 | Lev |
| 6,086,544 A | 7/2000 | Hibner et al. |
| 6,398,741 B2 | 6/2002 | Niizeki et al. |
| 6,942,669 B2 | 9/2005 | Kurc |
| 6,990,982 B1 | 1/2006 | Bonutti |
| 7,115,100 B2 | 10/2006 | McRury et al. |
| 7,442,171 B2 | 10/2008 | Stephens et al. |
| 7,611,473 B2 | 11/2009 | Boock et al. |
| 7,674,263 B2 | 3/2010 | Ryan |
| 8,858,546 B2 | 10/2014 | Hall et al. |
| 2003/0060862 A1 | 3/2003 | Goble |
| 2004/0078090 A1 | 4/2004 | Binette et al. |
| 2004/0193071 A1 | 9/2004 | Binette et al. |
| 2005/0038520 A1 | 2/2005 | Binette et al. |
| 2005/0113736 A1 | 5/2005 | Orr et al. |
| 2005/0125077 A1 | 6/2005 | Harmon et al. |
| 2005/0171504 A1* | 8/2005 | Miller .......................... 604/506 |
| 2007/0005084 A1* | 1/2007 | Clague et al. ................ 606/159 |
| 2007/0270893 A1* | 11/2007 | Pikus et al. .................. 606/159 |
| 2008/0071385 A1 | 3/2008 | Binette et al. |
| 2008/0214955 A1 | 9/2008 | Speeg et al. |
| 2008/0234715 A1 | 9/2008 | Pesce et al. |
| 2008/0243028 A1 | 10/2008 | Howard et al. |
| 2008/0311219 A1 | 12/2008 | Gosiewska et al. |
| 2010/0160819 A1 | 6/2010 | Parihar et al. |
| 2011/0282337 A1 | 11/2011 | Hall et al. |

FOREIGN PATENT DOCUMENTS

| | | |
|---|---|---|
| WO | WO 01/76680 | 10/2001 |
| WO | WO 02/47561 | 6/2002 |
| WO | WO 2008/042987 | 4/2008 |
| WO | WO 2009/017445 | 2/2009 |

OTHER PUBLICATIONS

International Search Report dated Sep. 6, 2011 for Application No. PCT/US2011/036249.
International Search Report dated Oct. 20, 2011 for Application No. PCT/US2011/036255.
Written Opinion dated Sep. 6, 2011 for Application No. PCT/US2011/036249.
Written Opinion dated Oct. 20, 2011 for Application No. PCT/US2011/036255.

* cited by examiner

INSTRUMENT FOR DEBRIDING FISTULA AND APPLYING THERAPEUTIC CELLS

BACKGROUND

Fistulae can occur for a variety of reasons, such as, from a congenital defect, as a result of inflammatory bowel disease such as Crohn's disease, some sort of trauma, or as a side effect from a surgical procedure. Additionally, several different types of fistulae can occur in humans, for example, urethro-vaginal fistulae, vesico-vaginal fistulae, tracheo-esophageal fistulae, gastrointestinal fistulae, for example gastrocutaneous, enterocutaneous and colocutaneous fistulae, and any number of anorectal fistulae such as recto-vaginal fistula, recto-vesical fistulae, recto-urethral fistulae, and recto-prostatic fistulae. When fistulas form, they can track between intestinal segments or between an intestinal segment and other organs (e.g., bladder, vagina, etc.), adjacent tissue, or the skin. Fistulas are classified as internal when they communicate with adjacent organs (e.g., entero-enteric and rectovaginal fistulas, etc.) and external when they communicate with the dermal surface (e.g., enterocutaneous, peristomal and perianal fistulas, etc.).

Promoting and improving tissue healing around the fistula opening and in the fistula tract may be an important aspect of fistulae medical treatments. For instance, promoting and improving tissue healing may lead to quicker recovery times and lessen the opportunity for infection, particularly in a post-surgical context. Some advancements in the medical arts pertaining to systems, methods, and devices to promote and improve tissue healing in patients aim to add active biological components (e.g., tissue particles, stem cells, other types of cells, etc.) to a wound site (e.g., surgical site, accidental trauma site, etc.) or other defect site (e.g., caused by disease or other condition, etc.) to promote tissue regeneration or accelerate tissue healing. When adding biological components to a site, such components may be added independently or as part of a specifically designed matrix or other mixture depending on the condition being treated and goals of the treatment. Some examples of cell-based therapy technology are disclosed in U.S. Pub. No. 2008/0311219, entitled "Tissue Fragment Compositions for the Treatment of Incontinence," published Dec. 18, 2008, now abandoned, the disclosure of which is incorporated by reference herein. Additional examples of cell-based therapy technology are disclosed in U.S. Pub. No. 2004/0078090, entitled "Biocompatible Scaffolds with Tissue Fragments," published Apr. 22, 2004, now abandoned, the disclosure of which is incorporated by reference herein. Additional examples of cell-based therapy technology are disclosed in U.S. Pub. No. 2008/0071385, entitled "Conformable Tissue Repair Implant Capable of Injection Delivery," published Mar. 20, 2008, issued as U.S. Pat. No. 7,875,296 on Jan. 25, 2011, the disclosure of which is incorporated by reference herein.

Regardless of how the active biological components are delivered or applied to a site, the biological components must first be obtained and prepared. One approach for obtaining such biological components is to harvest the desired components from a healthy tissue specimen (e.g., in an adult human). Examples of devices and associated methods for collecting and processing harvested tissue are disclosed in U.S. Pub. No. 2004/0193071, entitled "Tissue Collection Device and Methods," published Sep. 30, 2004, issued as U.S. Pat. No. 7,794,408 on Sep. 14, 2010, the disclosure of which is incorporated by reference herein. Additional examples of devices and associated methods for collecting and processing harvested tissue are disclosed in U.S. Pub. No. 2005/0038520, entitled "Method and Apparatus for Resurfacing an Articular Surface," published Feb. 17, 2005, the disclosure of which is incorporated by reference herein. Additional examples of devices and associated methods for collecting and processing harvested tissue are disclosed in U.S. Pat. No. 7,611,473, entitled "Tissue Extraction and Maceration Device," issued Nov. 3, 2009, the disclosure of which is incorporated by reference herein. Additional examples of devices and associated methods for collecting and processing harvested tissue are disclosed in U.S. Pub. No. 2008/0234715, entitled "Tissue Extraction and Collection Device," published Sep. 25, 2008, issued as U.S. Pat. No. 8,034,003 on Oct. 11, 2011, the disclosure of which is incorporated by reference herein. Additional examples of devices and associated methods for processing harvested tissue are disclosed in U.S. Pub. No. 2005/0125077, entitled "Viable Tissue Repair Implants and Methods of Use," published Jun. 9, 2005, issued as U.S. Pat. No. 7,901,461 on Mar. 8, 2011, the disclosure of which is incorporated by reference herein. Additional examples of devices and associated methods for collecting and processing harvested tissue are disclosed in U.S. Pat. No. 5,694,951, entitled "Method for Tissue Removal and Transplantation," issued Dec. 9, 1997, the disclosure of which is incorporated by reference herein. Additional examples of devices and associated methods for collecting and processing harvested tissue are disclosed in U.S. Pat. No. 6,990,982, entitled "Method for Harvesting and Processing Cells from Tissue Fragments," issued Jan. 31, 2006, the disclosure of which is incorporated by reference herein. Additional examples of devices and associated methods for collecting and processing harvested tissue are disclosed in U.S. Pat. No. 7,115,100, entitled "Tissue Biopsy and Processing Device," issued Oct. 3, 2006, the disclosure of which is incorporated by reference herein.

Once harvested and suitably processed (e.g., incorporated with a scaffold, etc.), biological material such as tissue fragments may be applied to a wound site or other type of site within the human body in a variety of ways. Various methods and devices for applying such biological material are disclosed in one or more of the U.S. patent references cited above. Additional methods and devices for applying such biological material are disclosed in U.S. Pub. No. 2005/0113736, entitled "Arthroscopic Tissue Scaffold Delivery Device," published May 26, 2005, issued as U.S. Pat. No. 8,673,021 on Mar. 18, 2014, the disclosure of which is incorporated by reference herein.

While a variety of devices and techniques may exist for harvesting, processing, and applying biological components from a tissue specimen, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings. In the drawings, like numerals represent like elements throughout the several views.

Figure 1:
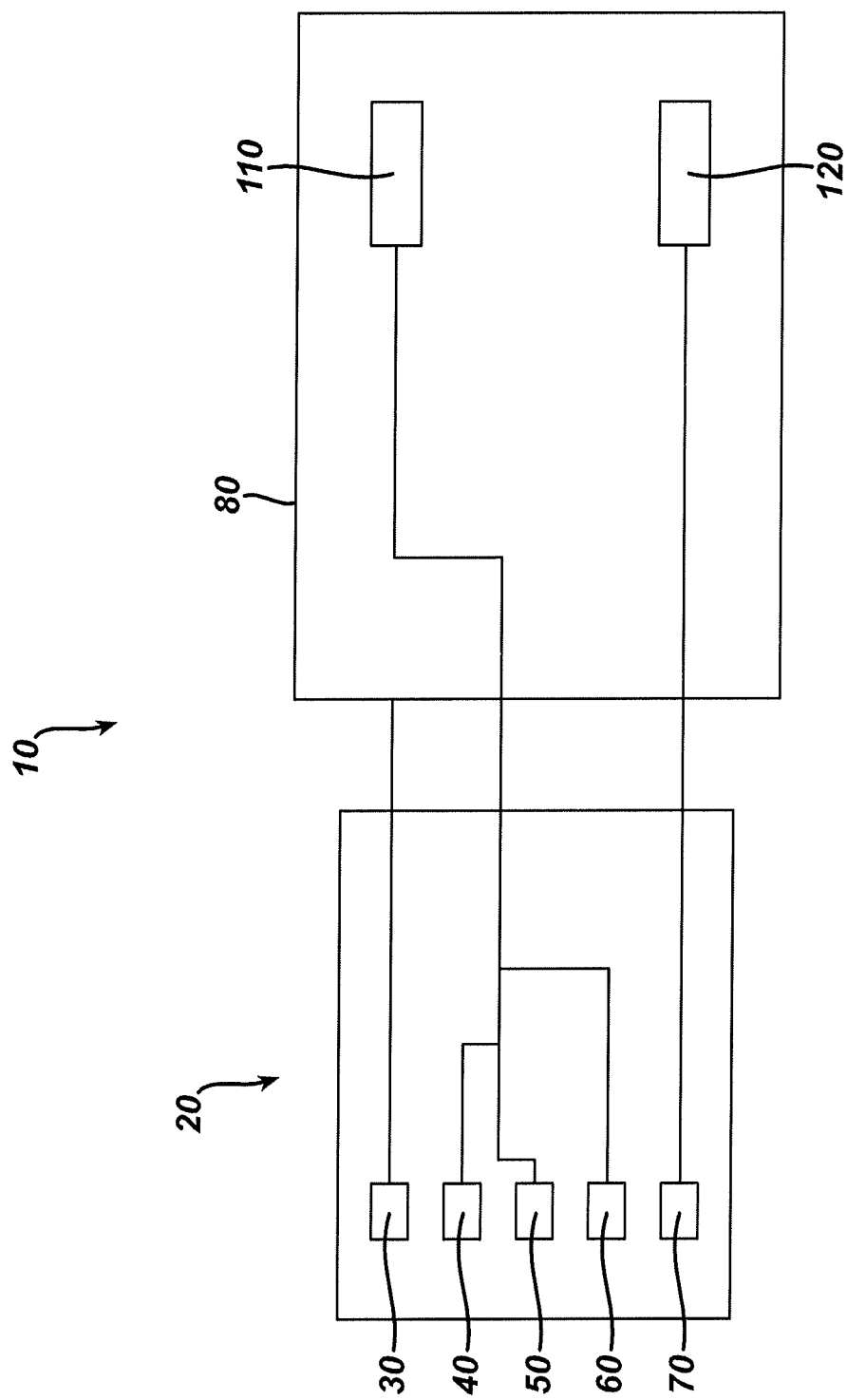
FIG. 1 depicts a block schematic view of an exemplary treatment system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples should not be used to limit the scope of the present invention. Other features, aspects, and advantages of the versions disclosed herein will become apparent to those skilled in the art from the following description, which is by way of illustration, one of the best modes contemplated for carrying out the invention. As will be realized, the versions described herein are capable of other different and obvious aspects, all without departing from the invention. Accordingly, the drawings and descriptions should be regarded as illustrative in nature and not restrictive.

I. Overview of Exemplary Treatment Compositions, Devices, and Methods

Examples described herein include devices that are operable to harvest tissue, mince or morcellate tissue, mix tissue particles with other medical fluid components, and/or dispense a medical fluid at a target site in a patient. As described in greater detail below, the medical fluid may include any of a variety of biocompatible materials that accelerate tissue healing, promote tissue regeneration, and/or provide other results. As used herein, the terms "tissue treatment composition," "tissue repair composition," "therapeutic mixture," and "medical fluid" should be read interchangeably. It should also be understood that a tissue treatment composition or medical fluid as referred to herein may have any suitable consistency, including but not limited to the consistency of a slurry.

A medical fluid as referred to herein may be derived from any biocompatible material, including but not limited to synthetic or natural polymers. The consistency of the medical fluid may be viscous, or gel-like, that of a slurry composed of microparticles, or any other suitable consistency. By way of example only, any fluid consistency that may permit injection through a catheter may be used. The medical fluid may also provide adhesive characteristics, such that once it is injected at a target site (e.g., into a fistula), the fluid coagulates or gels (e.g., allowing for a plug to be retained within a fistula). The medical fluid of the present example is also able to support cell migration and proliferation such that healing at a target site in a patient can occur. The fluid is suitable to be mixed with biological materials. Examples of medical fluid components include but are not limited to thrombin, platelet poor plasma (PPP) platelet rich plasma (PRP), starch, chitosan, alginate, fibrin, polysaccharide, cellulose, collagen, gelatin-resorcin-formalin adhesive, oxidized cellulose, mussel-based adhesive, poly (amino acid), agarose, amylose, hyaluronan, polyhydroxybutyrate (PHB), hyaluronic acid, poly(vinyl pyrrolidone) (PVP), poly(vinyl alcohol) (PVA), polylactide (PLA), polyglycolide (PGA), polycaprolactone (PCL), and their copolymers, VICRYL® (Ethicon, Inc., Somerville, N.J.), MONOCRYL material, PANACRYL (Ethicon, Inc., Somerville, N.J.), and/or any other material suitable to be mixed with biological material and introduced to a wound or defect site, including combinations of materials. Other suitable compounds, materials, substances, etc., that may be used in a medical fluid will be apparent to those of ordinary skill in the art in view of the teachings herein.

By way of example only, one or more components in a medical fluid or tissue treatment composition may comprise at least one viable tissue fragment having one or more viable cells that, once applied, can proliferate and integrate with tissue at a target site in a patient. For instance, viable cells may migrate out of a tissue particle and populate a scaffold material, which may be positioned at a target site in a patient. Such tissue fragments may have been harvested from the same patient in whom they are reapplied; or may have been harvested from another person or source. The tissue fragments may comprise autogenic tissue, allogenic tissue, xenogenic tissue, mixtures of any of the foregoing, and/or any other type(s) of tissue. The tissue fragments may include, for example, one or more of the following tissues or tissue components: stem cells, cartilage tissue, meniscal tissue, ligament tissue, tendon tissue, skin tissue, muscle tissue (e.g., from the patient's thigh, etc.), periosteal tissue, pericardial tissue, synovial tissue, fat tissue, bone marrow, bladder tissue, umbilical tissue, embryonic tissue, vascular tissue, blood and combinations thereof. Of course, any other suitable type of tissue may be used, including any suitable combination of tissue types. In some versions, the type of tissue used is selected from a tissue type most resembling the tissue at, near, or surrounding the target site (e.g., fistula, etc.).

Tissue for providing at least one viable tissue fragment may be obtained using any of a variety of tissue biopsy devices or using other types of tissue harvesting devices or techniques. Exemplary biopsy devices include those taught in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2007/0118048, entitled "Remote Thumbwheel for a Surgical Biopsy Device," published May 24, 2007, issued as U.S. Pat. No. 7,442,171 on Oct. 28, 2008; U.S. Pub. No. 2008/0214955, entitled "Presentation of Biopsy Sample by Biopsy Device," published Sep. 4, 2008; U.S. Non-Provisional patent application Ser. No. 12/337,942, entitled "Biopsy Device with Central Thumbwheel," filed Dec. 18, 2008, published as U.S. Pub. No. 2010/0160819 on Jun. 24, 2010, now abandoned; and U.S. Non-Provisional patent application Ser. No. 12/483,305, entitled "Tetherless Biopsy Device with Reusable Portion," filed Jun. 12, 2009, issued as U.S. Pat. No. 8,206,316 on Jun. 26, 2012. The disclosure of each of the above-cited U.S. Patents, U.S. Patent Application Publications, and U.S. Non-Provisional Patent Applications is incorporated by reference herein. Such biopsy devices may be used to extract a plurality of tissue specimens from one or more sites in a single patient. It should also be understood that any suitable device described in any other reference that is cited herein may be used to harvest tissue. Additional examples of devices that may be used to harvest tissue will be described in greater detail below. Other examples will be apparent to those of ordinary skill in the art in view of the teachings herein. Tissue harvesting sites may include the same sites in which tissue is reapplied as part of a treatment. In addition or in the alternative, tissue may be harvested from one site and then reapplied at some other site as part of a treatment. In some versions, the tissue is reapplied in the same patient from whom the tissue was originally harvested. In some other versions, the tissue is applied in a patient who is different from the patient from whom the tissue was originally harvested.

A tissue specimen may be obtained under aseptic conditions, and then processed under sterile conditions to create a suspension having at least one minced, or finely divided, tissue fragment. In other words, harvested tissue may be diced, minced or morcellated, and/or otherwise processed. Harvested tissue specimens may be minced and otherwise processed in any of a variety of ways. For instance, examples of tissue mincing and processing are described in U.S. Pub. No. 2004/0078090, now abandoned, the disclosure of which is incorporated by reference herein. Alternatively, merely exemplary non-conventional devices and techniques that may be used to mince and process tissue will be described in greater detail below, while other examples will be apparent to those of ordinary skill in the art in view of the teachings herein. In order to ensure viability of the tissue, agitators or other features of a mincing and/or mixing device may be designed to sever and mix (rather than crush or compress) the tissue. In some settings, tissue specimens may be minced and/or mixed in a standard cell culture medium, either in the presence or absence of serum. Tissue fragments may also be contacted with a matrix-digesting enzyme to facilitate cell migration out of an extracellular matrix surrounding the cells. Suitable matrix-digesting enzymes that may be used in some settings include, but are not limited to, collagenase, chondroitinase, trypsin, elastase, hyaluronidase, peptidase, thermolysin, and protease. The size of each tissue fragment may vary depending on the target location, method for delivering the treatment composition to the target site, and/or based on various other considerations. For example, the tissue fragment size may be chosen to enhance the ability of regenerative cells (e.g., fibroblasts) in the tissue fragments to migrate out of the tissue fragments, and/or to limit or prevent the destruction of cell integrity. In some settings, ideal tissue fragments are between approximately 200 microns and approximately 500 microns in size. As another merely illustrative example, ideal tissue fragments may be sized within the range of approximately 0.05 $mm^3$ and approximately 2 $mm^3$; or more particularly between approximately 0.05 $mm^3$ and approximately 1 $mm^3$. Of course, various other tissue fragment sizes may be ideal in various different settings.

In some versions, a medical fluid may comprise minced tissue fragments suspended in a biocompatible carrier. Suitable carriers may include, for example, a physiological buffer solution, a flowable gel solution, saline, and water. In the case of gel solutions, the tissue repair composition may be in a flowable gel form prior to delivery at the target site, or may form a gel and remain in place after delivery at the target site. Flowable gel solutions may comprise one or more gelling materials with or without added water, saline, or a physiological buffer solution. Suitable gelling materials include biological and synthetic materials. Exemplary gelling materials include the following: proteins such as collagen, collagen gel, elastin, thrombin, fibronectin, gelatin, fibrin, tropoelastin, polypeptides, laminin, proteoglycans, fibrin glue, fibrin clot, platelet rich plasma (PRP) clot, platelet poor plasma (PPP) clot, self-assembling peptide hydrogels, Matrigel or atelocollagen; polysaccharides such as pectin, cellulose, oxidized regenerated cellulose, chitin, chitosan, agarose, or hyaluronic acid; polynucleotides such as ribonucleic acids or deoxyribonucleic acids; other materials such as alginate, cross-linked alginate, poly(N-isopropylacrylamide), poly(oxyalkylene), copolymers of poly(ethylene oxide)-poly(propylene oxide), poly(vinyl alcohol), polyacrylate, or monostearoyl glycerol co-Succinate/polyethylene glycol (MGSA/PEG) copolymers; and combinations of any of the foregoing. In addition to providing a flowable carrier solution for tissue fragments, a gelling agent(s) may also act as an adhesive that anchors the tissue repair composition at the target site. In some versions, an additional adhesive anchoring agent may be included in the tissue repair composition or medical fluid. Also, one or more cross-linking agents may be used in conjunction with one or more gelling agents in order to cross-link the gelling agent.

The concentration of tissue fragments in a carrier and/or one or more medical fluid components may vary depending on the target site location, method for delivering the treatment composition to the target site, and/or for various other reasons. By way of example, the ratio of tissue fragments to carrier (by volume) may be in the range of about 2:1 to about 6:1, or in the range of about 2:1 to about 3:1. The medical fluid may also include one more additional healing agents, such as biological components that accelerate healing and/or tissue regeneration. Such biological components may include, for example, growth factors, proteins, peptides, antibodies, enzymes, platelets, glycoproteins, hormones, cytokines, glycosaminoglycans, nucleic acids, analgesics, viruses, isolated cells, or combinations thereof. The medical fluid may further include one or more additional treatment components that prevent infection, reduce inflammation, prevent or minimize adhesion formation, and/or suppress the immune system. In some versions where a scaffold is used in conjunction with a tissue treatment composition, one or more of these additional biological components or additional treatment components may be provided on and/or within the scaffold. Similarly, in some versions where a scaffold plug is used in conjunction with a tissue repair composition, one or more of these additional biological components or additional treatment components may be provided on and/or within the scaffold plug. Some examples described herein may also include one or more adhesive agents in conjunction with viable tissue fragments.

As noted above, the harvested tissue may be combined with a scaffold material and/or other substances as part of a medical fluid, as described herein, for administration to the patient. To the extent that tissue is incorporated with a scaffold material, it should be understood that any suitable material or combination of materials may be used to provide a scaffold. By way of example only, scaffold material may include a natural material, a synthetic material, a bioabsorbable polymer, a non-woven polymer, other types of polymers, and/or other types of materials or combinations of materials. Examples of suitable biocompatible materials include starch, chitosan, cellulose, agarose, amylose, lignin, hyaluronan, alginate, hyaluronic acid, fibrin glue, fibrin clot, collagen gel, gelatin-resorcin-formalin adhesive, platelet rich plasma (PRP) gel, platelet poor plasma (PPP) gel, Matrigel, Monostearoyl Glycerol co-Succinate (MGSA), Monostearoyl Glycerol co-Succinate/polyethylene glycol (MGSA/PEG) copolymers, laminin, elastin, proteoglycans, polyhydroxybutyrate (PHB), poly(vinyl pyrrolidone) (PVP), polylactide (PLA), polyglycolide (PGA), polycaprolactone (PCL), and their copolymers, non-woven VICRYL® (Ethicon, Inc., Somerville, N.J.), MONOCRYL material, fibrin, non-woven poly-L-lactide, and non-woven PANACRYL (Ethicon, Inc., Somerville, N.J.). Polymers may include aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, poly(propylene fumarate), polyurethane, poly(ester urethane), poly(ether urethane), and blends and copolymers thereof Suitable synthetic polymers for use in examples described herein may also include biosynthetic polymers based on sequences found in collagen, laminin, glycosaminoglycans, elastin, thrombin, fibronectin, starches, poly(amino acid), gelatin, alginate, pectin, fibrin, oxidized cellulose, chitin, chitosan, tropoelastin, hyaluronic acid, silk, ribonucleic acids, deoxyribonucleic acids, polypeptides, proteins, polysaccharides, polynucleotides, and combinations thereof Other suitable materials or combinations of materials that may be used will be apparent to those of ordinary skill in the art in view of the teachings herein. It should also be understood that tissue mixed with a scaffold material may have any suitable particle size, and that the resulting mixture may at least initially have the consistency of a slurry or have any other suitable consistency. In some versions, the tissue particles include an effective amount of viable cells that can migrate out of the tissue particle and populate the scaffold. The term "viable," as used herein, should be understood to include a tissue sample having one or more viable cells.

In some versions, one or more components in a medical fluid or tissue treatment composition comprise one or more healing agents that promote tissue regeneration at a target site (e.g., within a fistula) and/or accelerate tissue healing at the target site. Healing agents may include any of a variety of biocompatible materials that accelerate tissue healing and/or promote tissue regeneration. Such biological components may include, for example, growth factors, proteins, peptides, antibodies, enzymes, platelets, glycoproteins, hormones, cytokines, glycosaminoglycans, nucleic acids, analgesics, viruses, isolated cells, or combinations thereof The medical fluid may further include one or more additional treatment components that prevent infection, reduce inflammation, prevent or minimize adhesion formation, and/or suppress the immune system. In some versions where a scaffold is used in conjunction with a tissue treatment composition, one or more of these additional biological components or additional treatment components may be provided on and/or within the scaffold. Some examples described herein may also include one or more adhesive agents in conjunction with viable tissue fragments.

Examples described herein relate to the repair (e.g., closing) of lumens in a patient, such as anal fistulas and other types of fistulas. In particular, examples described herein include devices used in at least part of a process to create and/or deliver tissue repair compositions or medical fluid into a lumen such as an anal fistula. It should be understood that anal fistulas and/or other types of fistulas may be relatively difficult to repair (e.g., close) in some settings. The goal of a surgical repair of an anal fistula may be to close the fistula with as little impact as possible on the sphincter muscles. In some settings, a tissue repair composition or medical fluid as described herein may be delivered into the fistula as a liquid composition, a flowable gel or paste, a scaffold plug, or a combination of the two or more of the foregoing (e.g., a porous scaffold plug loaded with a medical fluid composition, etc). Anal fistulas may also be repaired by injecting bioresorbable fibrin glue into the fistula that seals the fistula and promotes tissue growth across the fistula in order to provide permanent closure. Various bioresorbable plugs may also be used to repair anal fistulas. The plug may comprise, for example, collagen protein, tissue, stem cells, and/or other medical fluid components referred to herein; and the plug may be inserted into the fistula where it promotes tissue growth across the fistula as the plug dissolves. If desired, the plug may be secured in place using one or more fasteners and/or one or more adhesive agents. As another merely illustrative example, a medical fluid may be introduced within the fistula, and the medical fluid may eventually harden and then dissolve and/or be absorbed.

Prior to applying a medical fluid to a fistula, it may be desirable in some settings to debride the wall of a fistula (e.g., to remove epithelial cells, etc.), otherwise agitate the wall of the fistula, and/or otherwise treat the walls of the fistula. Merely illustrative examples of how the walls of a fistula may be treated and how a medical fluid may be applied in a fistula will be described in greater detail below. While examples herein are discussed in the context of an anorectal fistula, it should be understood that the following exemplary devices and techniques may be readily applied to various other types of fistulae. Similarly, while the present example relates to treatment of a fistula in a patient, it should also be understood that the following exemplary devices and techniques may be readily applied with respect to various other types of conditions in a patient. Other suitable ways in which the devices and techniques described herein may be used will be apparent to those of ordinary skill in the art in view of the teachings herein.

As used herein, the term "fluid communication" (or in some contexts "communication") means that there is a path or route through which fluid (gas, liquid or other flowable material) may flow between two components, either directly or through one or more intermediate components. Similarly, the term "conduit" encompasses a conduit within or integrated with a valve. In other words, fluid communication between two components means that fluid can flow from one component to another but does not exclude an intermediate component (e.g., a valve, etc.) between the two recited components that are in fluid communication. Similarly, two or more components may be in mechanical "communication" with each other even if intermediate components are interposed between those two or more components.

II. Exemplary Fistula Treatment System with Protruding Cutting Features

FIG. 1 shows components of an exemplary treatment system (10) in diagrammatic block form. As will be described in greater detail below, treatment system (10) may be used to debride a fistula and administer a therapeutic mixture of biological material to the fistula to treat the fistula. It should be understood, however, that treatment system (10) may be used in a variety of other ways and in a variety of other settings and procedures. As shown, treatment system (10) of the present example comprises a control unit (20), an outer sheath (80), an end effector (110), and a probe (120). While treatment system (10) includes a probe (120) in the present example, it will be appreciated that probe (120) is merely optional and may be omitted in some versions if desired. End effector (110) and probe (120) will be described in more detail below. In the example illustrated in FIG. 1, control unit (20) comprises a plurality of components. Specifically, control unit (20) includes a vacuum source (30), an actuator (40), a medical fluid reservoir (50), a saline reservoir (60), and a power source (70). Vacuum source (30) is in communication with outer sheath (80). Actuator (40) and medical fluid reservoir (50) are in communication with end effector (110). Power source (70) is in communication with probe (120). It will be appreciated that each of these components are merely optional, and one or more of them may be substituted, supplemented, or even omitted in some versions.

Treatment system (10) shown in FIG. 1 may be configured to not only harvest or obtain tissue specimens to be used in the treatment of a wound site (e.g., surgical site, accidental trauma site, etc.) or other defect site (e.g., caused by disease or other condition, etc.), but also to deliver a medical fluid to promote and improve tissue healing. Specifically, treatment system (10) may allow a user to debride a fistula, harvest one or more tissue specimens from the tissue surrounding the fistula, mix the tissue specimens with a biocompatible material, and inject the medical fluid (e.g. the mixture of harvested tissue specimens and biocompatible/scaffold material) within the interior cavity of the fistula using a single device. Some versions may also include a probe that enhances the functionality of the system by allowing a user to seal one or more openings in the fistula. The probe may be integrated together with the debriding/harvesting/injecting device to provide a single device configured to accomplish all of these functions, such as in the examples shown in FIGS. 6-13 and FIGS. 16-18, or the probe may be a separate device to be used in conjunction with a debriding/harvesting/injecting device as part of a single overall treatment system.

As shown in FIG. 1, control unit (20) comprises a plurality of optional components. In some versions, control unit (20) may comprise a single control module configured to house, provide controls for, and/or provide access to one or more of the components shown in FIG. 1. Control unit (20) may also comprise controls configured to manage positioning and operation of end effector (110) and probe (120). In some other versions, control unit (20) may comprise two or more modules, where each module houses, provides controls for, and/or provides access to one or more of the components. Each module may comprise a suitable interface to allow a user to control or manipulate one or more associated components. The components may be grouped together in any suitable fashion within the module(s). Control unit (20) may comprise a suitable combination of portable, hand-held, and fixed modules, although this is not required. Suitable constructions and configurations for control unit (20) will be apparent to those of ordinary skill in the art in view of the teachings herein.

As shown in FIG. 1, control unit (20) comprises vacuum source (30), which is in fluid communication with outer sheath (80). Vacuum source (30) may comprise a conventional vacuum pump (not shown) and any other suitable components as will be apparent to those of ordinary skill in the art in view of the teachings herein. While vacuum source (30) is shown as being part of control module (20) in the present example, it should be understood that an external vacuum source may be used in addition to or in lieu of a vacuum source (30) in control module (20). In the illustrated version, vacuum source (30) is configured to communicate a vacuum through outer sheath (80). In an alternate version, vacuum source (30) may be in fluid communication with end effector (110) such that a vacuum is communicated through a distal opening in end effector (110), although such a distal opening is not required; or through one or more other apertures in end effector (110), such as cutting features (116, 316, 516a, 516b, 616a, 616b, 716, 816) shown in FIGS. 2-3 and 7-18 and described below. Vacuum source (30) may be coupled with outer sheath (80) or end effector (110) via tubing, conduits, or any other connection means suitable to communicate a vacuum.

Vacuum source (30) may be activated using a vacuum control (not shown), such as a foot pedal switch, a trigger, a button, or some other suitable type of activation feature coupled with vacuum source (30) to provide selective activation of vacuum source (30). Vacuum source (30) may further be configured to be actuated in conjunction with one or more other components of control unit (20). By way of example only, vacuum source (30) may be configured to be automatically activated when actuator (40) is initiated; or, alternatively, vacuum source (30) may be configured to be automatically activated when probe (120) is actuated to seal an opening. Various suitable ways in which such automatic/selective activation may be provided will be apparent to those of ordinary skill in the art in view of the teachings herein. It should be understood from the teachings herein that vacuum source (30) may be used before a treatment procedure is initiated, during a treatment procedure (e.g., on an "as needed basis" during use of the end effector and/or probe), or at any other suitable time.

In the illustrated example, control unit (20) further comprises actuator (40), which is in mechanical communication with end effector (110). In the present example, actuator (40) is operable to rotate end effector (100). In some other versions, actuator (40) is also operable to translate end effector (100) longitudinally, in addition to or in lieu of rotating end effector (100). Actuator (40) may be configured to cause end effector (110) to rotate in more than one rotational direction and/or translate in more than one longitudinal direction, although this is not required. Actuator (40) may be in mechanical communication with end effector (110) via a rotational shaft/member, a longitudinally translating shaft/member, and/or any other structure suitable to transfer motion created by actuator (40) to end effector (110).

Actuator (40) may comprise a motorized device and/or a pneumatic device, including but not limited to a conventional DC motor, an AC motor, a pneumatic motor, a pneumatic linear actuator, an electromechanical linear actuator, a piezoelectric oscillator, an electroactive polymer actuator, an electromagnetic actuator, and/or a variety of other types of movement-inducing devices. In some versions, actuator (40) may be activated using an actuator control (not shown), such as a foot pedal switch, a trigger, a button, or some other suitable type of activation feature coupled with actuator (40) to provide selective activation of actuator (40). Actuator (40) may further be configured to be actuated in conjunction with one or more other components of control unit (20). By way of example only, actuator (40) may be configured to be automatically activated when vacuum source (30) is initiated. Various suitable ways in which such automatic/selective activation may be provided will be apparent to those of ordinary skill in the art in view of the teachings herein. In some other versions, actuator (40) may comprise a manual device, including but not limited to a knob, a crank, a handle or any other suitable manual movement-inducing device in mechanical communication with end effector (110).

As shown in FIG. 1, control unit (20) further comprises a medical fluid reservoir (50). Medical fluid reservoir (50) may comprise any suitable container or containers that is/are configured to retain a medical fluid and/or one or more components that are operable to create a medical fluid. While medical fluid reservoir (50) is shown as being part of control module (20) in the present example, it should be understood that an external source of medical fluid may be used in addition to or in lieu of a medical fluid reservoir (50) in control module (20). The medical fluid in reservoir (50) may include any one or more of the various medical fluid components referred to herein, among others. In the illustrated example, medical fluid reservoir (50) is in fluid communication with end effector (110) such that the medical fluid contained in medical fluid reservoir (50) may be communicated to a wound or defect site via end effector (110). Control unit (20) may comprise controls (not shown) configured to manage distribution, and, in some versions, mixing, of the medical fluid. The medical fluid may be communicated to the wound or defect site via an interior lumen in end effector (110) that is in communication with medical fluid reservoir (50) at a proximal end and that is in communication with one or more apertures in end effector (110) at a distal end. The apertures in end effector (110) may comprise one or more of the following: a distal opening in the distal end of end effector (110), a plurality of cutting features in end effector (110), or at least one distribution aperture configured to allow the medical fluid to be distributed into the cavity of the fistula. In some such versions, a medical fluid ready for distribution (e.g. pre-mixed tissue specimens and biocompatible scaffold material) may be deposited within medical fluid reservoir (50) and subsequently communicated to the wound or defect site.

In some versions, system (10) is configured to provide two-way fluid communication between medical fluid reservoir (50) and end effector (110). In some such versions, medical fluid reservoir (50) may receive tissue specimens harvested by end effector (110) to dice, mince, and/or mix the tissue specimens with either a biocompatible material or a pre-mixed medical fluid, in addition to communicating the medical fluid from medical fluid reservoir (50) to end effector as described above. In some such versions, the tissue specimens may be communicated from end effector (110) into medical fluid reservoir (50) via a vacuum initiated by vacuum source (30) and/or any other suitable means for conveying the tissue specimens from end effector (110) to medical fluid reservoir (50). The two-way fluid communication may be provided via a single lumen or conduit or via two distinct lumens or conduits between medical fluid reservoir (50) and end effector (110). Medical fluid reservoir (50) may comprise an agitator (not shown) configured to mix tissue specimens with the biocompatible material or pre-mixed medical fluid present in medical fluid reservoir, although this is not required.

As shown in FIG. 1, control unit (20) further comprises a saline reservoir (60).

Saline reservoir (60) may comprise any suitable container configured to retain saline for distribution via one or more components of system (10). Control unit (20) may comprise one or more controls configured to manage distribution of the saline. While saline reservoir (60) is shown as being part of control module (20) in the present example, it should be understood that an external saline source may be used in addition to or in lieu of a saline reservoir (60) in control module (20). In the present example, saline reservoir (60) is in fluid communication with end effector (110) such that the saline contained in saline reservoir (60) may be communicated to a wound or defect site via end effector (110). The saline may be used to flush debrided pieces of tissue from the interior of end effector (110) and/or the interior cavity of the fistula. Of course, other suitable substances in addition to or in place of saline may be contained in saline reservoir (60) and used to flush debrided pieces of tissue from the interior of end effector (110) and/or the target site (e.g. the interior cavity of the fistula). Similar to medical fluid reservoir (50), the saline may be communicated to the wound or defect site via an interior lumen in end effector (110) that is in communication with saline reservoir (60) at a proximal end and that is in communication with one or more apertures in end effector (110) at a distal end. The apertures in end effector (110) may comprise one or more of the following: a distal opening in the distal end of end effector (110), a plurality of cutting features in end effector (110), or at least one distribution aperture configured to allow the saline to be distributed into the interior cavity of the fistula. The saline may be communicated to the wound or defect site via the same interior lumen in end effector (110) as the medical fluid; or, alternatively, end effector (110) may comprise a first lumen to allow communication of the medical fluid and a second lumen to allow communication of the saline.

In some other versions (not shown), saline reservoir (60) may be in fluid communication with outer sheath (80). In some such versions, the saline, or other substance(s) contained in saline reservoir (60), may be communicated through outer sheath (80) into the interior cavity of the fistula.

In the illustrated example, control unit (20) further comprises a power source (70). Power source (70) is configured to provide electrical power to probe (120), which will be described in more detail below. Power source (70) may comprise a rechargeable battery, a non-rechargeable battery, any other type of battery, a conventional AC power source, or any other suitable piece of power generating equipment. In some versions, power source (70) may also be configured to provide electrical power to other components of system (10), including but not limited to actuator (40), vacuum source (30), and/or end effector (110).

Figure 2:
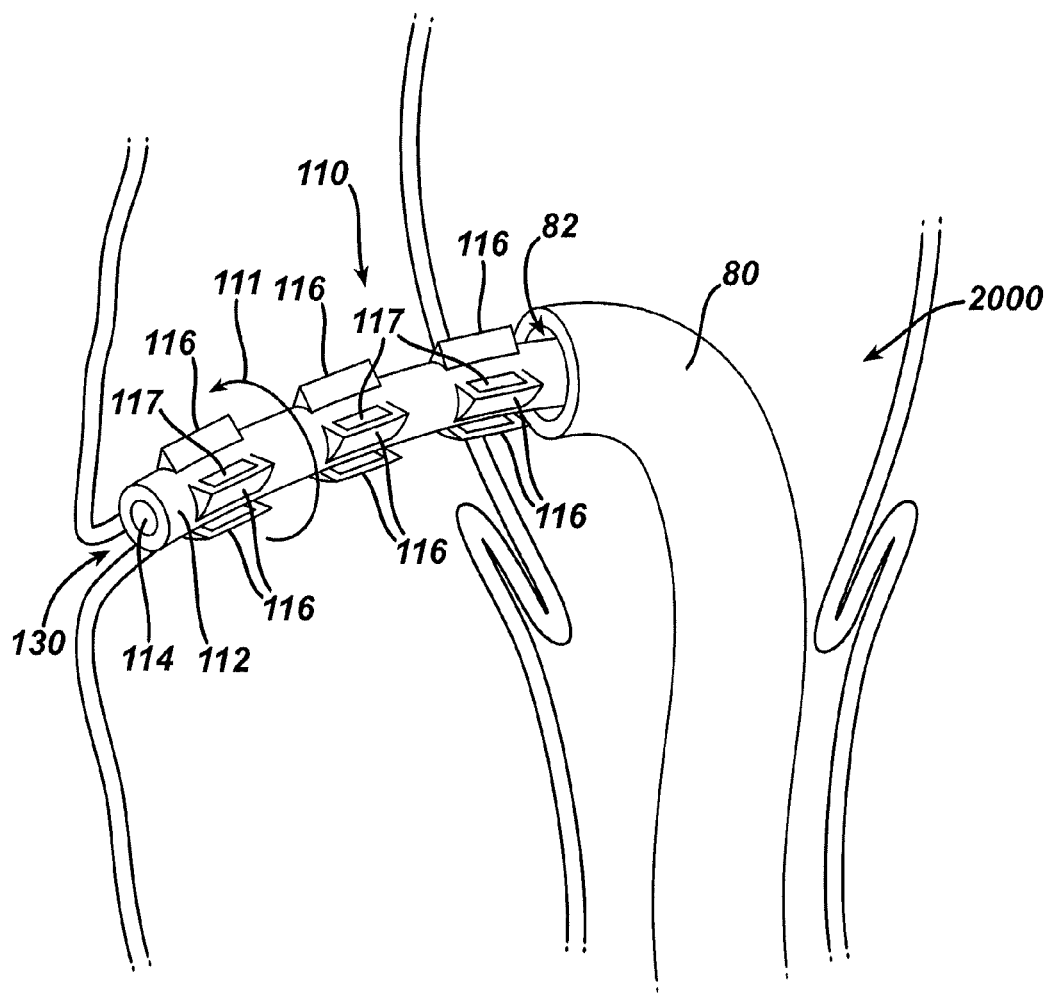
FIG. 2 depicts a perspective view of an exemplary end effector and an exemplary outer sheath of the treatment system of FIG. 1, inserted into a fistula via a rectum.
Figure 3:
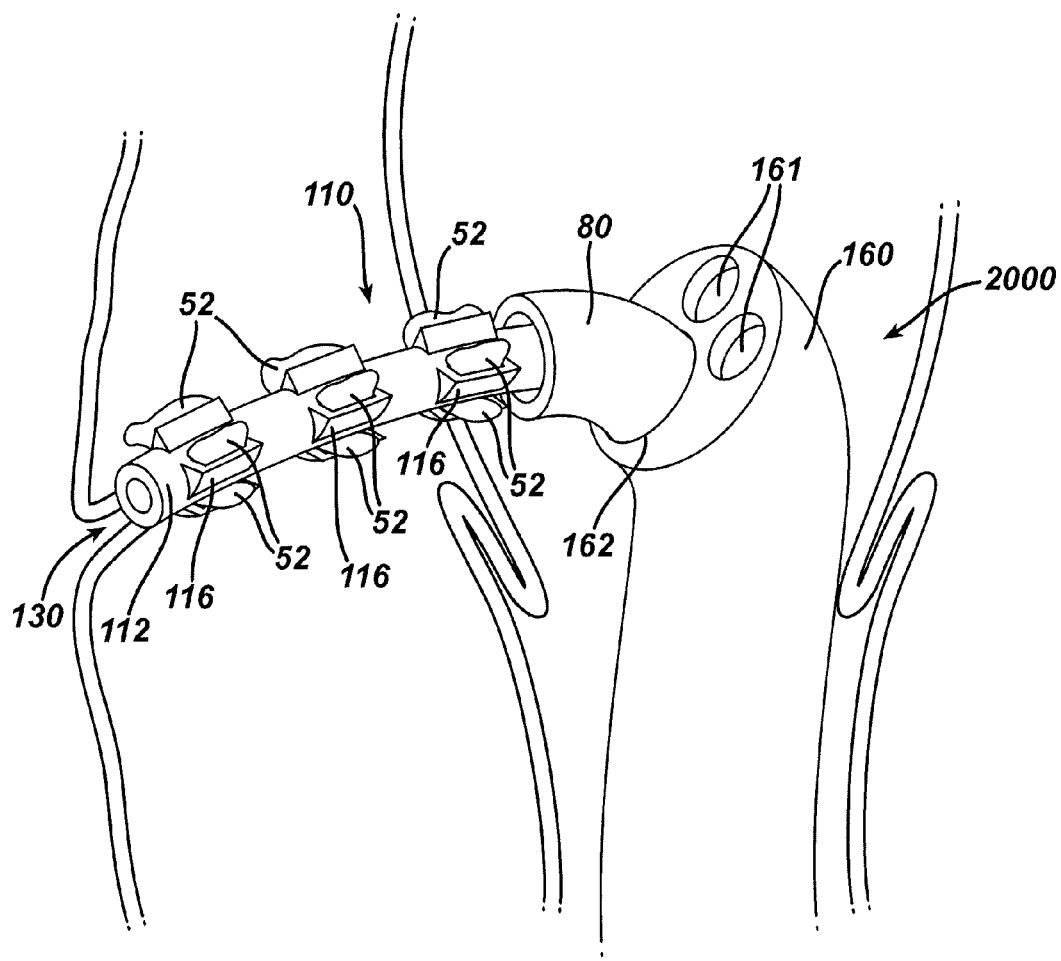
FIG. 3 depicts a perspective view of the end effector and outer sheath of FIG. 2 being used to inject a medical fluid into the fistula.
Figure 4:
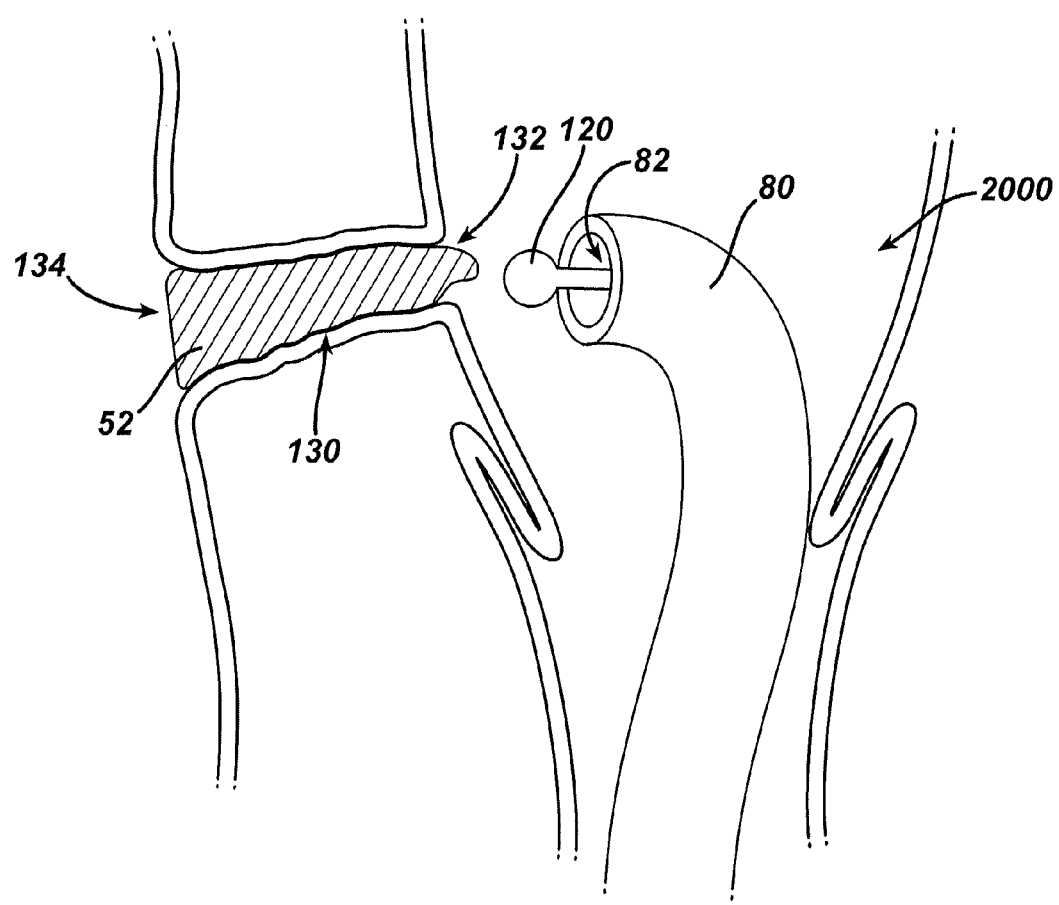
FIG. 4 depicts a perspective view of an exemplary probe and an exemplary outer sheath of the treatment system of FIG. 1, positioned to seal a proximal end of the fistula.
Figure 5:
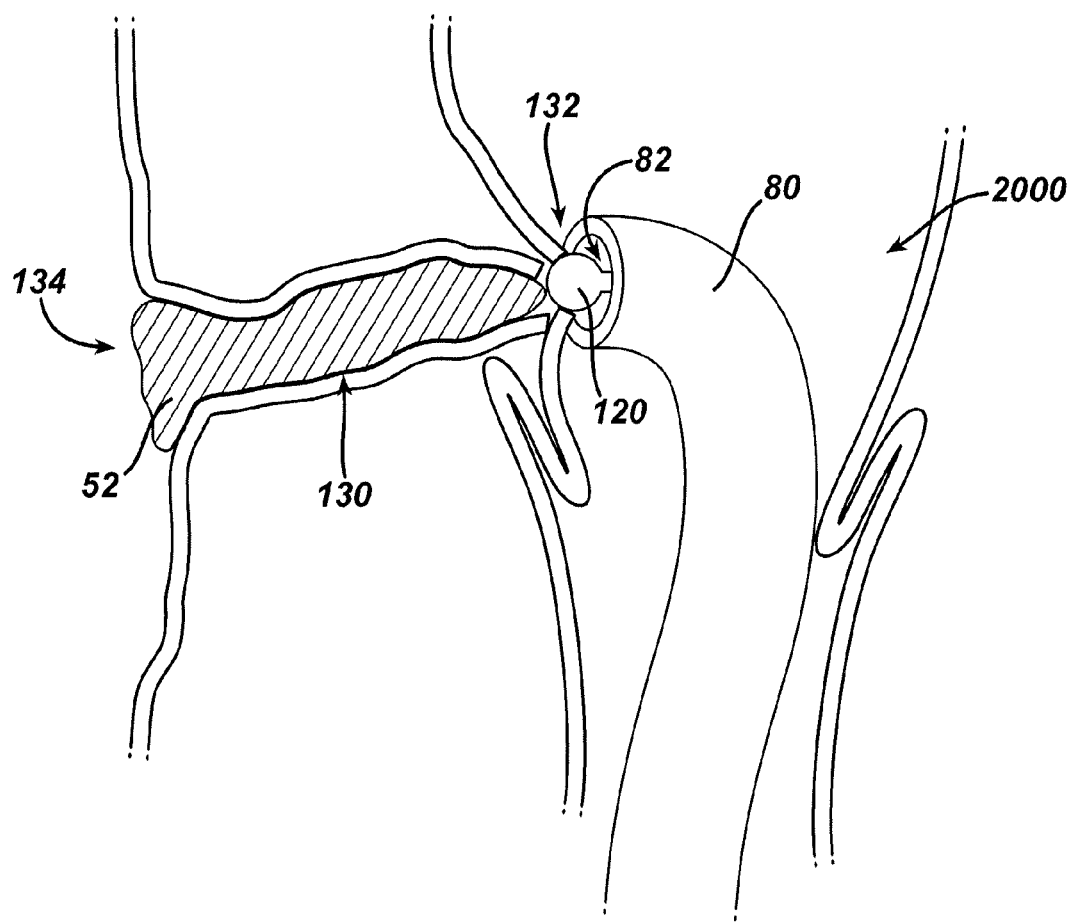
FIG. 5 depicts the probe and outer sheath of FIG. 4 being used to seal the proximal end of the fistula.

FIGS. 2-5 depict exemplary components of system (10) during various stages of treating a fistula. In particular, FIG. 2 depicts one example of an end effector (110) being used to debride the interior surface of a fistula (130). Debriding the interior of the fistula may remove epithelial cells from the interior surface of the fistula, which may facilitate healing and/or acceptance of a therapeutic mixture. As shown in FIGS. 2, 4, and 5, outer sheath (80) may be inserted directly into a patient's rectum (2000) via the anus (not shown) such that the distal opening (82) of outer sheath (80) is adjacent to the target wound or defect site. Alternatively, as shown in FIG. 3, outer sheath (80) may be inserted into a working channel (162) of an endoscope (160) that is positioned in the patient's rectum (2000). Outer sheath (80) may extend along the length of endoscope (160) such that distal opening (82) of outer sheath (80) is adjacent to the target site. Endoscope (160) may provide additional channels (161) to allow for the use of additional instruments, including but not limited to cameras and lights. The user may be able to extend and retract outer sheath (80) within the patient and/or along the length of endoscope (160). This may be accomplished manually, with the aid of motorized or pneumatic extension means, or in any other suitable fashion.

In the illustrated version, the target site is a fistula (130). It should be understood, however, that system (10) may be used with various other types of target sites. As shown, end effector (110) protrudes through distal opening (82) of outer sheath (80) and into the interior cavity of fistula (130). End effector (110) may be extended and retracted through outer sheath (80) manually by the user using any suitable mechanism. Alternatively, system (10) may comprise a motorized or pneumatic means for extending and retracting end effector (110). It will be appreciated that end effector (110) may be initially retracted relative to outer sheath (80) during initial insertion of outer sheath (80) into the patient, and that end effector (110) may be subsequently exposed within the patient via extension of end effector (110) relative to outer sheath (80), retraction of outer sheath (80) relative to end effector (110), or some combination thereof.

As shown in FIGS. 2-3, end effector (110) comprises a hollow cylindrical body (112) having a longitudinal axis, a distal opening (114), and a plurality of cutting features (116). In some other versions, distal opening (114) may be omitted and the distal tip of end effector (110) may be closed. Cylindrical body (112) may define an interior lumen that is in fluid communication with medical fluid reservoir (50) and/or saline reservoir (60) as described above. In the illustrated example, cutting features (116) comprise tangential projections, each projection having an opening (117) that is in communication with the interior lumen of end effector (110). End effector (110) may comprise any suitable number of cutting features (116) and cutting features (116) may be arranged in any configuration suitable to provide the desired functionality. Cutting features (116) may each have at least one cutting edge that is configured to debride and/or slice through tissue. Alternatively, cutting features (116) may comprise a debriding surface that is sharpened or abrasive to remove tissue cells (e.g., epithelial cells, etc.) from the interior surface of fistula (130) during debriding, and a harvesting edge that is sharpened to slice through tissue surrounding the interior cavity of fistula (130) to obtain tissue specimens during harvesting. Cutting features (116) may thus comprise openings, projections, protuberances, notches, and/or any other structure suitable to debride a tissue surface and/or harvest tissue specimens. Cutting features (116) may be configured to provide a cutting action similar to that of a cheese grater on the interior surface of fistula (130) during debriding; and on tissue surrounding the interior cavity of fistula (130) during harvesting.

Figure 22:
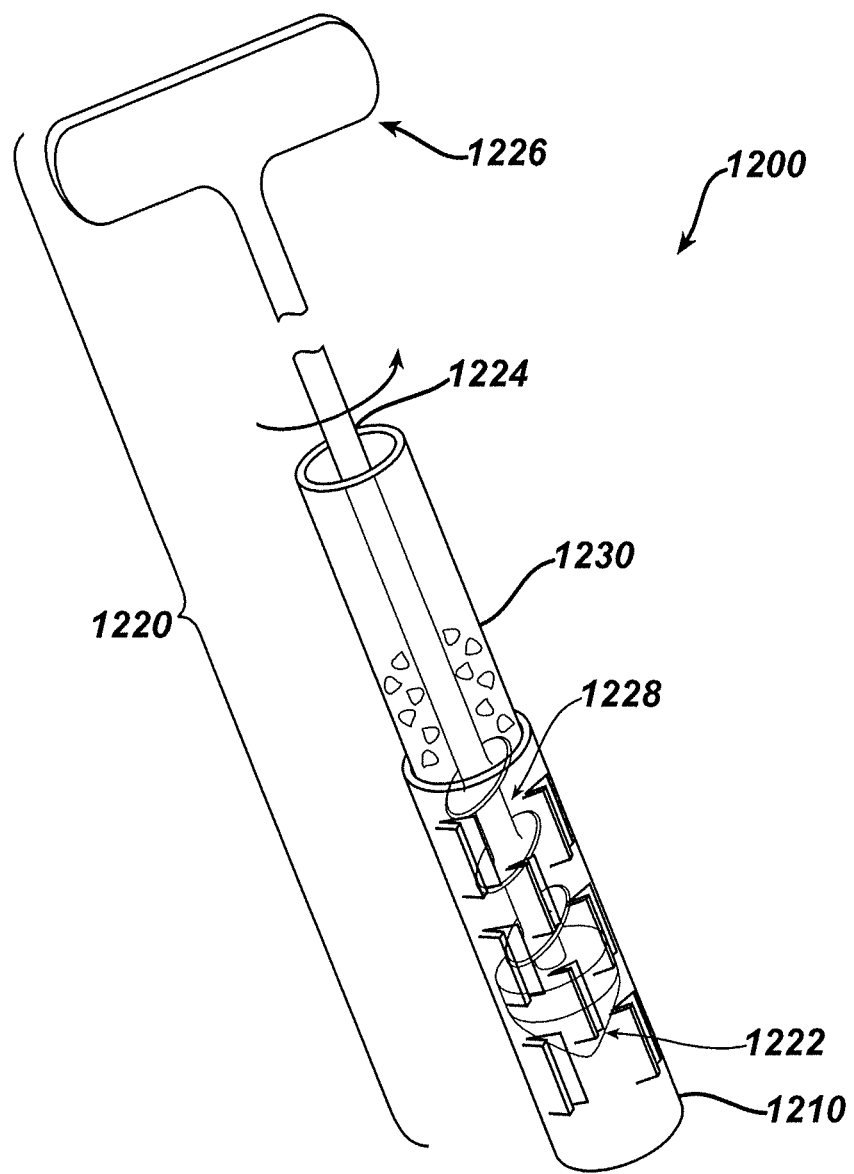
FIG. 22 depicts a perspective view of an instrument comprising another exemplary alternative plunger.

In the illustrated example, cutting features (116) are configured to both debride the interior surface of fistula (130) and harvest tissue specimens from tissue that defines the wall of fistula (130). Alternatively, cutting features (116) may be configured to only debride or only harvest. In versions where cutting features (116) are configured to harvest tissue specimens, such cutting features (116) and associated openings (117) may be configured to slice and capture tissue specimens of any desired shape and dimensions. In some versions, one or more cutting features (116) and one or more associated openings (117) extend longitudinally along a substantial part of the length of end effector (110), or even the full length of end effector (110). Such a cutting feature (116) and opening (117) may thus be configured to cut and receive a tissue specimen that is long and thin. In some such versions, end effector (110) or some other component of system (10) may include one or more features that are operable to dice/mince such a long thin tissue specimen. Such dicing/mincing may be performed within the interior of end effector (110), within the interior of outer sheath (80), and/or elsewhere within system (10). An example of such a feature is shown in FIG. 22 and is described in greater detail below, tough other suitable examples of such a feature will be apparent to those of ordinary skill in the art in view of the teachings herein. In addition to dicing/mincing the tissue specimen, the feature may also mix the diced/minced tissue with the medical fluid and/or provide other functionality.

As shown, cutting features (116) are oriented such that debriding and harvesting may be accomplished by rotating end effector (110) in a counter-clockwise direction, as indicated by arrow (111). Of course, in some other versions, the orientation of cutting features (116) may be reversed such that debriding and harvesting may be accomplished via clockwise rotation of end effector (110). In still further versions, at least one of the plurality of cutting features (116) may be oriented in a first direction requiring counter-clockwise rotation for debriding and/or harvesting, while at least one other one of the plurality of cutting features (116) is oriented in a second direction requiring clockwise rotation for debriding and/or harvesting. In some such versions, actuator (40) may be configured to selectively rotate end effector (110) in both counter-clockwise and clockwise directions. It should also be understood that cutting features (116) may be configured to debride and/or harvest tissue through longitudinal reciprocating motion of end effector (110), in addition to or in lieu of providing debriding and/or harvesting through rotational motion of end effector (110). Various suitable configurations and operabilities for cutting features (116) will be apparent to those of ordinary skill in the art in view of the teachings herein.

The interior surface of fistula (130) may be debrided by inserting end effector (110) into the interior cavity of fistula (130), as shown in FIG. 2, and rotating end effector (110) in a counter-clockwise direction (viewed from the distal end of end effector (110) toward the proximal end). Once the interior surface of fistula (130) has been adequately debrided, the loose pieces of debrided tissue may be flushed from end effector (110) and from the interior cavity of fistula (130) by delivering saline through the interior lumen of end effector (110) into the interior cavity of fistula (130). The saline may be distributed to the interior cavity of fistula (130) via distal opening (114) and/or openings (117) in cutting features (116). Of course, the flushing step is optional and may be omitted in some versions or procedures. In some other versions, instead of flushing debrided tissue with saline, the debrided tissue may be removed from the site using a vacuum communicated to the site through end effector (110), outer sheath (80), or some combination thereof. The vacuum may be initiated by vacuum source (30) or another suitable vacuum source. Using the example shown in FIG. 2, after debriding, and flushing in some versions, a user may harvest, or obtain, tissue specimens from newly exposed tissue surrounding the interior cavity of fistula (130) by rotating end effector (110) in a counter-clockwise direction. Debriding may remove a layer of epithelial cells from the interior surface of fistula (130), thereby exposing a layer of endothelial cells for harvesting. Harvesting tissue specimens comprising substantially endothelial cells, as opposed to specimens comprising substantially epithelial cells or a combination of the two types of cells, for use in the medical fluid may be desirable for some treatment methods, although it is not required.

During harvesting, cutting features (116) may come into contact with and slice through tissue surrounding the interior cavity of fistula (130), creating tissue specimens that are captured via openings (117) in cutting features (116) and deposited into the interior lumen of end effector (110). In some versions, the tissue specimens are communicated proximally toward medical fluid reservoir (50) using a vacuum initiated by vacuum source (30) and communicated through the interior lumen of end effector (110). Again, saline may also be provided at the site of fistula (130) to assist in proximal transport of tissue specimens toward medical fluid reservoir (50). Other versions may incorporate other means for communicating tissue specimens proximally, including but not limited to a plunger, a vacuum initiated by a source other than vacuum source (30), or any other suitable device or method. Once the tissue specimens reach medical fluid reservoir (50), then the tissue specimens may be mixed with a substance contained within medical fluid reservoir (50). That substance may comprise a previously mixed medical fluid or a biocompatible material. By way of example only, the material mixed with harvested tissue specimens may provide a scaffold for the tissue specimens. It should also be understood that system (10) may include one or more features that are operable to dice, morcellate, and/or mince the harvested tissue specimens before and/or during mixing with a medical fluid and/or biocompatible material (e.g., scaffold material) in medical fluid reservoir (50). In still further versions, tissue specimens may remain contained within the interior lumen of end effector (110) as a substance is communicated distally from medical fluid reservoir (50). That substance may comprise a previously mixed medical fluid or a biocompatible material.

As shown in FIG. 3, a medical fluid (52) is distributed into the interior cavity of fistula (130). Specifically, in this version, medical fluid (52) is communicated through the interior lumen of end effector (110) and into fistula (130) via openings (117) in cutting features (116). In some versions, medical fluid (52) may be distributed into fistula (130) via distal opening (114) of end effector (110) in addition to or instead of being distributed via openings (117), but this is not required. Medical fluid (52) may be communicated from medical fluid reservoir (50) to end effector (110) using any suitable device or method, including but not limited to tubing and conduits, a piston or pump mechanism, etc.

End effector (110) may be retracted proximally and removed from the interior cavity of fistula (130) once a sufficient amount of medical fluid (52) has been delivered. Medical fluid (52) may expand to fill the interior cavity of fistula (130) although this is not necessarily required. In some versions, end effector (110) may be withdrawn entirely from outer sheath (80) to allow probe (120) to be inserted into outer sheath (80) and extended proximally toward the target site. In some other versions, probe (120) may be positioned co-axially within end effector (110), such that probe (120) may be exposed by retracting end effector (110) relative to probe (120) and/or by extending probe (120) relative to end effector (110) such that probe (120) protrudes from distal opening (114). It will therefore be appreciated that probe (120) may be exposed after insertion into a patient via extension of probe (120) relative to outer sheath (80), retraction of outer sheath (80) relative to end effector (110), extension of probe (120) relative to end effector (110), retraction of end effector (110) relative to probe (120), or some combination thereof.

As shown in FIGS. 4 and 5, probe (120) is extended through distal opening (82) of outer sheath (80) so that probe (120) is adjacent to proximal opening (132) of fistula (130), within rectum (2000). Probe (120) comprises a medical device configured to apply radio frequency (RF) energy to tissue in order to heat the tissue and induce coagulation of the tissue. For instance, probe (120) may comprise a monopolar RF device or a bipolar RF device. Control unit (20) may comprise suitable components required to provide the required energy via probe (120), including but not limited to circuit board(s), power source(s), and electrode(s). In some alternate versions, probe (120) may utilize a means for inducing coagulation of tissue other than RF energy. By way of example only, probe (120) may comprise a thermal heating device, a cryogenic device, an ultrasonic device, or any other suitable type of device. Various suitable ways in which probe (120) and associated components in control unit (20) may be configured will be apparent to those of ordinary skill in the art in view of the teachings herein.

In the treatment method depicted in FIG. 5, a vacuum is induced through outer sheath (80) as probe (120) and distal opening (82) are positioned adjacent to proximal opening (132) of fistula (130). In the illustrated example, the vacuum draws the tissue surrounding proximal opening (132) together and towards probe (120) to facilitate coagulation of the tissue and sealing of proximal opening (132). The RF energy may be transmitted to the tissue as it comes into contact with probe (120). Once proximal opening (132) has been satisfactorily sealed, the user may remove outer sheath (80) and probe (120) from the patient's rectum (2000) by retracting outer sheath (80) and/or probe (120) proximally. In alternate treatment methods, probe (120) may be used to seal distal opening (134) of fistula prior to injection of medical fluid (52). The sealing of distal opening (134) may occur at any point prior to injection of medical fluid (52) (e.g. prior to debriding, after debriding but prior to harvesting, etc.). While end effector (110) is introduced into fistula (130) via rectum (2000) in the present example, it should be understood that end effector (110) may be introduced into fistula (130) externally (e.g., such that end effector (110) is inserted in distal opening (134) and urged toward rectum (2000) via fistula (130), etc.). Such an approach may be provided during an entire procedure in which system (10) is used or only during some parts of a procedure in which system (10) is used (e.g., such that end effector (110) is inserted in rectum (2000) during other parts of the procedure, etc.). Various other suitable ways in which system (10) may be used (in relation to a fistula (130) or otherwise) will be apparent to those of ordinary skill in the art in view of the teachings herein. Similarly, various ways in which components of system (10) may be provided, configured, and operable will be apparent to those of ordinary skill in the art in view of the teachings herein.

III. Exemplary Fistula Treatment System with Cutting Apertures

Figure 6:
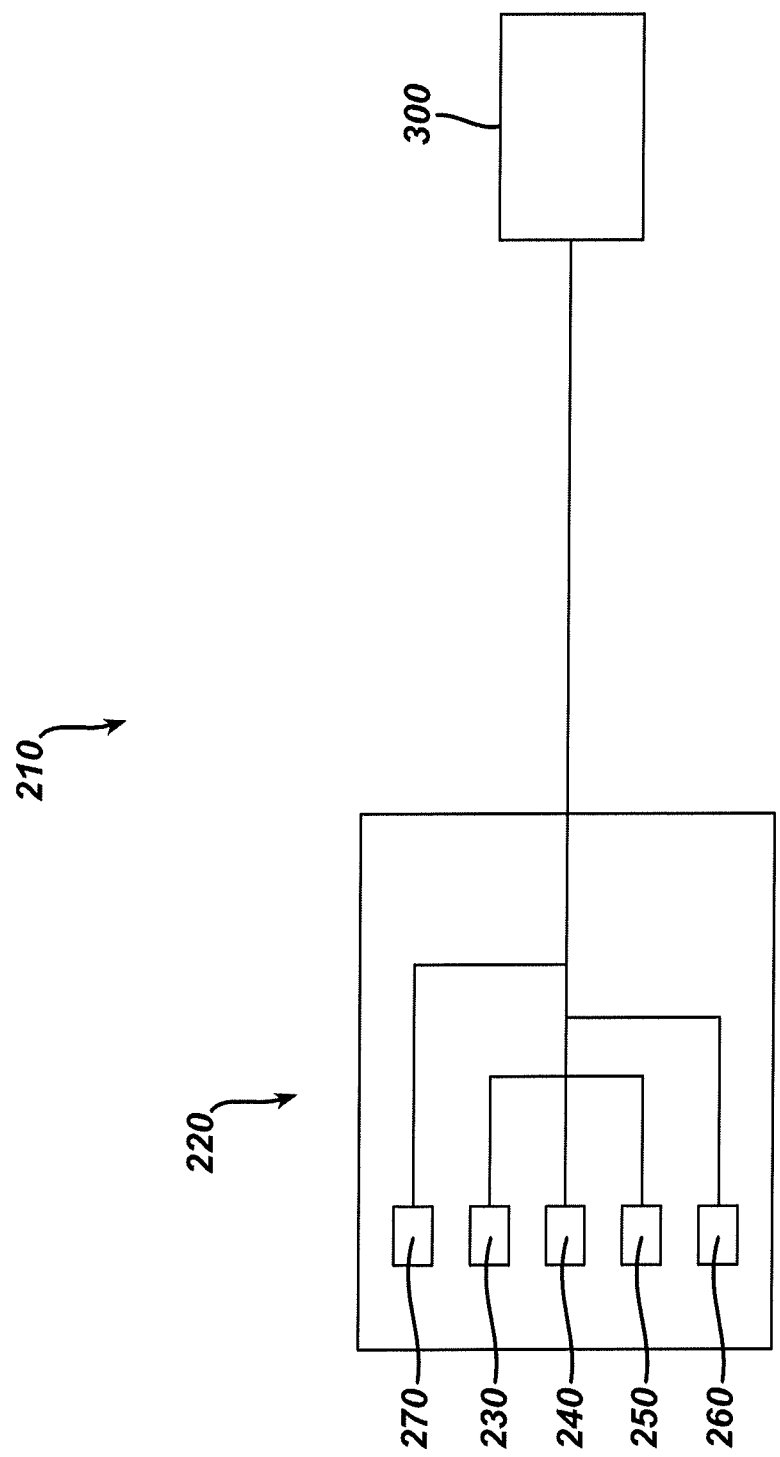
FIG. 6 depicts a schematic view of an exemplary alternative treatment system.
Figure 7:
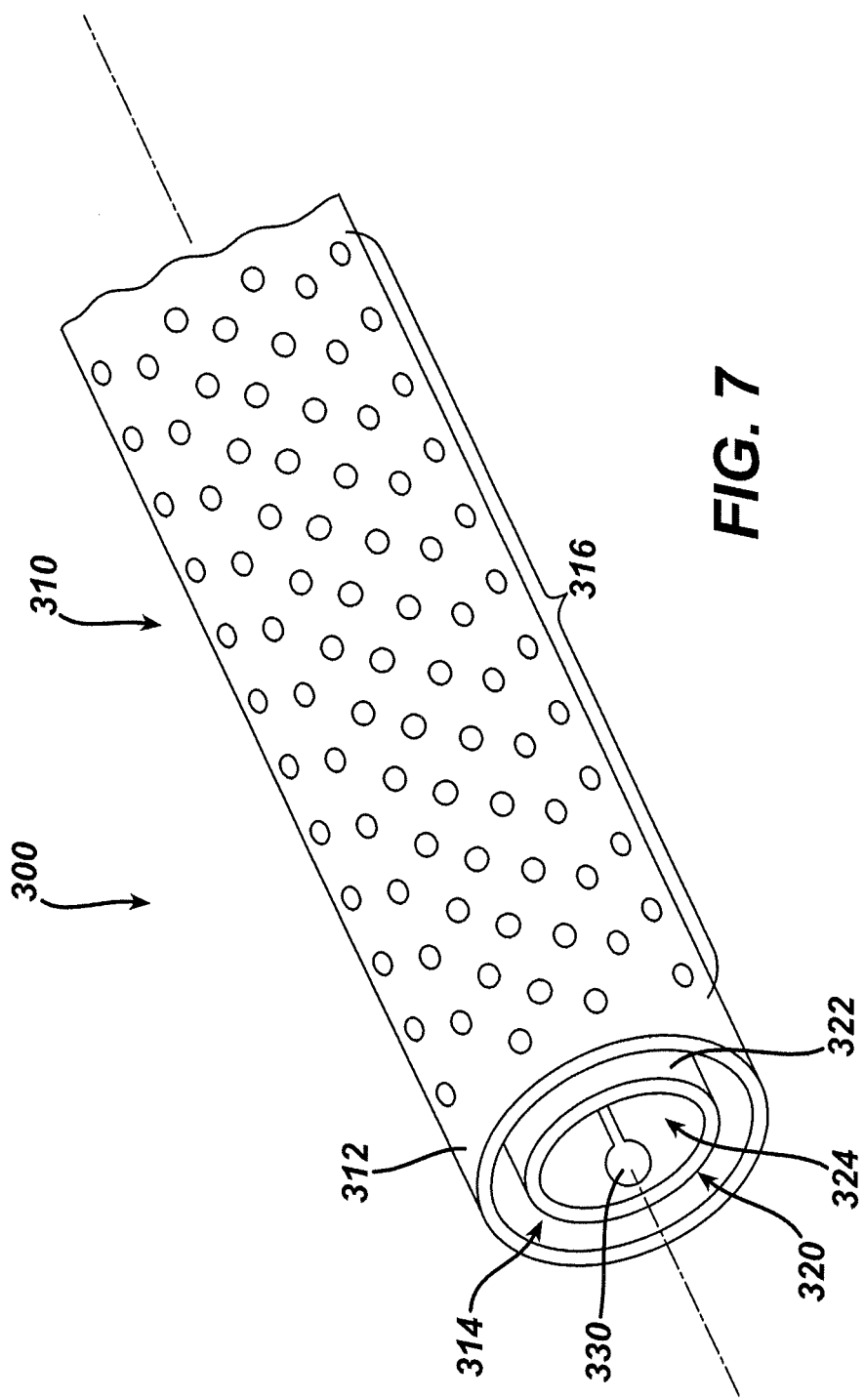
FIG. 7 depicts a perspective view of an exemplary instrument of the treatment system of FIG. 6.
Figure 8:
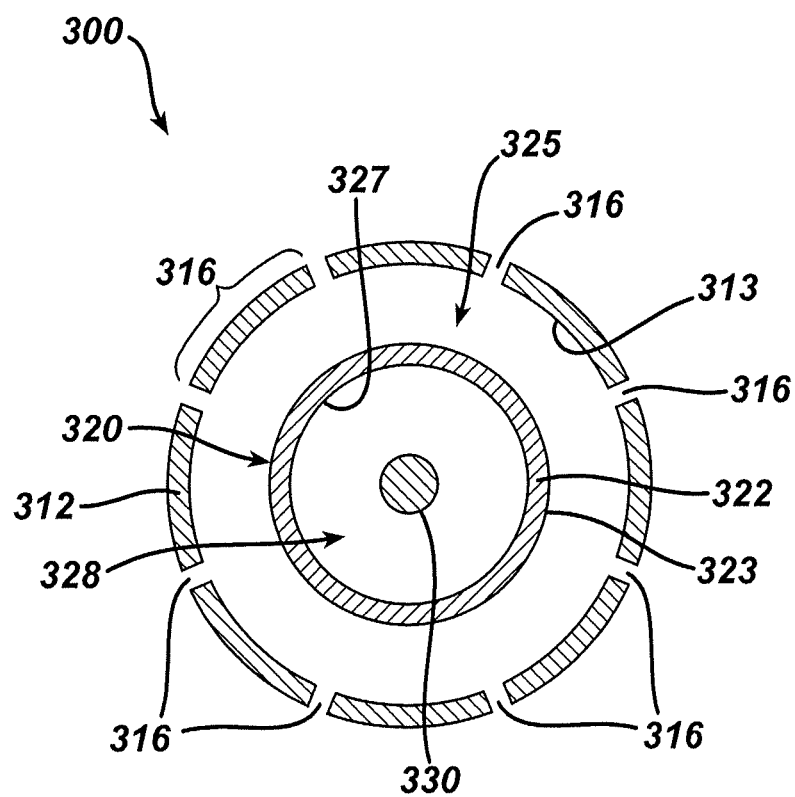
FIG. 8 depicts an end, cross-sectional view of the instrument of FIG. 7.

FIG. 6 shows components of another exemplary treatment system (210) in diagrammatic block form. As will be described in greater detail below, treatment system (210) may be used to debride a fistula and administer a therapeutic mixture of biological material to the fistula to treat the fistula. It should be understood, however, that treatment system (210) may be used in a variety of other ways and in a variety of other settings and procedures. As shown, treatment system (210) of this example comprises a control unit (220) and a treatment instrument (300). Treatment instrument (300) will be described in more detail below. In the example illustrated in FIG. 6 control unit (220) comprises a plurality of components. Specifically, control unit (220) includes a vacuum source (230), an actuator (240), a medical fluid reservoir (250), a saline reservoir (260), and a power source (270) in communication with treatment instrument (300). Treatment instrument (300), which will be described in more detail below, may comprise one or more components, including but not limited to an end effector, a vacuum cannula, and a probe. It will be appreciated that each of these components are merely optional, and one or more of them may be omitted in some versions.

Similar to treatment system (10) shown in FIG. 1 and described above, treatment system (210) may be configured to not only harvest or obtain tissue specimens to be used in the treatment of a target site, but also to deliver a medical fluid to promote and improve tissue healing. Treatment system (210), and more specifically treatment instrument (300), may allow a user to debride a fistula, harvest one or more tissue specimens from the tissue surrounding the fistula, mix the tissue specimens with a biocompatible material, and inject the medical fluid (e.g. a mixture of harvested tissue specimens and scaffold material) within the interior cavity of the fistula using a single device. Some versions may also include a probe that enhances the functionality of the system by allowing a user to seal one or more openings in the fistula. In the examples illustrated in FIGS. 6-13 and FIGS. 16-18, the probe is integrated together with the treatment instrument (300) to provide a single device configured to accomplish all of these functions. Of course, a probe may alternatively be provided as a separate device.

As shown in FIG. 6, control unit (220) comprises a plurality of optional components. Similar to control unit (20) described above, control unit (220) may comprise a single control module configured to house, provide controls for, and/or provide access to one or more of the components shown in FIG. 6. Control unit (220) may also comprise controls configured to manage positioning and operation of treatment instrument (300) and/or the individual components of treatment instrument (300), which will be described in more detail below. In some other versions, control unit (220) may comprise two or more modules, where each module houses, provides controls for, and/or provides access to one or more of the components. Each module may comprise a suitable interface to allow a user to control or manipulate one or more associated components. The components may be grouped together in any suitable fashion within the module(s). Control unit (220) may comprise a suitable combination of portable, hand-held, and fixed modules, although this is not required. Suitable constructions and configurations for control unit (220) will be apparent to those of ordinary skill in the art in view of the teachings herein.

As shown in FIG. 6, control unit (220) comprises vacuum source (230), which is in fluid communication with treatment instrument (300). Vacuum source (230) may comprise a conventional vacuum pump (not shown) and any other suitable components as will be apparent to those of ordinary skill in the art in view of the teachings herein. While vacuum source (230) is shown as being part of control module (220) in the present example, it should be understood that an external vacuum source may be used in addition to or in lieu of a vacuum source (230) in control module (220). In the illustrated version, vacuum source (230) is configured to communicate a vacuum through at least one portion or component of treatment instrument (300). In the example of treatment instrument (300) shown in FIGS. 7-13, vacuum source (230) is in fluid communication with vacuum cannula (320), such that a vacuum is communicated to the target site via vacuum channel (328). Vacuum source (230) may be coupled with treatment instrument (300) via tubing, conduits, or any other connection means suitable to communicate a vacuum.

Similar to vacuum source (30) described above, vacuum source (230) may be activated using a vacuum control (not shown), such as a foot pedal switch, a trigger, a button, or some other suitable type of activation feature coupled with vacuum source (230) to provide selective activation of vacuum source (230). Vacuum source (230) may further be configured to be actuated in conjunction with one or more other components of control unit (20). By way of example only, vacuum source (230) may be configured to be automatically activated when actuator (240) is initiated; or, alternatively, vacuum source (230) may be configured to be automatically activated when treatment instrument (300) is actuated to seal an opening. Various suitable ways in which such automatic/selective activation may be provided will be apparent to those of ordinary skill in the art in view of the teachings herein. It should be understood from the teachings herein that vacuum source (230) may be used before a treatment procedure is initiated, during a treatment procedure (e.g., on an "as needed basis" during use of the end effector and/or probe), or at any other suitable time.

In the illustrated example, control unit (220) further comprises actuator (240), which is in mechanical communication with treatment instrument (300). In the present example, actuator (240) is operable to rotate at least one component of treatment instrument (300), such as end effector (310) shown in FIGS. 7-13. In some other versions, actuator (240) is also operable to translate end effector (310) longitudinally, in addition to or in lieu of rotating end effector (310). Actuator (240) may be configured to cause end effector (310) to rotate in more than one rotational direction and/or translate in more than one longitudinal direction, although this is not required. Actuator (240) may be in mechanical communication with treatment instrument (300) via a rotational shaft/member, a longitudinally translating shaft/member, or any other structure suitable to transfer motion created by actuator (240) to treatment instrument (300).

Similar to actuator (40) described above, actuator (240) may comprise a motorized device and/or a pneumatic device, including but not limited to a conventional DC motor, an AC motor, a pneumatic motor, a pneumatic linear actuator, an electromechanical linear actuator, a piezoelectric oscillator, an electroactive polymer actuator, an electromagnetic actuator, and/or a variety of other types of movement-inducing devices. In some versions, actuator (240) may be activated using an actuator control (not shown), such as a foot pedal switch, a trigger, a button, or some other suitable type of activation feature coupled with actuator (240) to provide selective activation of actuator (240). Actuator (240) may further be configured to be actuated in conjunction with one or more other components of control unit (220). By way of example only, actuator (240) may be configured to be automatically activated when vacuum source (230) is initiated. Various suitable ways in which such automatic/selective activation may be provided will be apparent to those of ordinary skill in the art in view of the teachings herein. In some other versions, actuator (240) may comprise a manual device, including but not limited to a knob, a crank, a handle or any other suitable manual movement-inducing device in mechanical communication with treatment instrument (300).

As shown in FIG. 6, control unit (220) further comprises a medical fluid reservoir (250). Medical fluid reservoir (250) may be substantially similar to medical fluid reservoir (50) described above. Accordingly, the details regarding the medical fluid contained therein, etc., will not be repeated here. In the illustrated example, medical fluid reservoir (250) is in fluid communication with treatment instrument (300) such that the medical fluid contained in medical fluid reservoir (250) may be communicated to a wound or defect site via one or more components of treatment instrument (300). Control unit (220) may comprise controls (not shown) configured to manage distribution, and, in some versions, mixing, of the medical fluid. The medical fluid may be communicated to the target site via an interior lumen within treatment instrument (300), such as delivery channel (325), that is in communication with medical fluid reservoir (250) at a proximal end and that is in communication with one or more apertures in treatment instrument (300) at a distal end. The apertures in treatment instrument (300) will be described in more detail below. In some versions, a medical fluid ready for distribution (e.g. pre-mixed tissue specimens and biocompatible scaffold material) may be deposited within medical fluid reservoir (250) and subsequently communicated to the target site.

Similar to one example of system (10) described above, system (210) may be configured to provide two-way fluid communication between medical fluid reservoir (240) and treatment instrument (300). In some such versions, medical fluid reservoir (250) may receive tissue specimens harvested by treatment instrument (300) to dice, mince, and/or mix the tissue specimens with either a biocompatible material or a pre-mixed medical fluid, in addition to communicating the medical fluid from medical fluid reservoir (250) to treatment instrument (300) as described above. In some such versions, the tissue specimens may be communicated from treatment instrument (300) into medical fluid reservoir (250) via a vacuum initiated by vacuum source (230) and/or any other suitable means for conveying the tissue specimens from treatment instrument (300) to medical fluid reservoir (250). The two-way fluid communication may be provided via a single lumen or conduit or two distinct lumens or conduits between medical fluid reservoir (250) and treatment instrument (300). Medical fluid reservoir (250) may comprise an agitator (not shown) configured to mix tissue specimens with the biocompatible material or pre-mixed medical fluid present in medical fluid reservoir, although this is not required.

As shown in FIG. 6, control unit (220) further comprises a saline reservoir (260). Saline reservoir (60) may be substantially similar to saline reservoir (60) described above. Control unit (220) may comprise one or more controls configured to manage distribution of the saline. In this version, saline reservoir (260) is in fluid communication with treatment instrument (300) such that the saline contained in saline reservoir (260) may be communicated to a wound or defect site via treatment instrument (300). The saline may be used to flush debrided pieces of tissue from the interior of treatment instrument (300) and/or the target site (e.g. the interior cavity of the fistula). Of course, other suitable substances in addition to or in place of saline may be contained in saline reservoir (260) and used to flush debrided pieces of tissue from the interior of treatment instrument (300) and/or the target site. Similar to medical fluid reservoir (250), the saline may be communicated to the target site via an interior lumen within treatment instrument (300), such as delivery channel (325), that is in communication with saline reservoir (260) at a proximal end and that is in communication with one or more apertures in treatment instrument (300) at a distal end. The apertures in treatment instrument (300) will be described in more detail below. The saline may be communicated to the target site via the same interior lumen in treatment instrument (300) as the medical fluid. Alternatively, treatment instrument (300) may comprise a first interior lumen to allow communication of the medical fluid and a second interior lumen to allow communication of the saline.

In the illustrated example, control unit (220) further comprises a power source (270). Power source (270) is configured to provide electrical power to one or more components of treatment instrument (300), which will be described in more detail below. By way of example only, in some versions wherein treatment instrument comprises a probe, such as probe (330) shown in FIGS. 7-13, power source (270) may be configured to provide electrical power to the probe. Power source (270) may comprise a rechargeable battery, a non-rechargeable battery, any other type of battery, a conventional AC power source, or any other suitable piece of power generating equipment. In some versions, power source (270) may also be configured to provide electrical power to other components of system (210), including but not limited to actuator (240), vacuum source (230), and/or other components of treatment instrument (300), such as end effector (310) in the examples shown in FIGS. 7-13.

As shown in FIGS. 7-13, treatment instrument (300) of the present example is a multi-functional instrument configured to debride a tissue surface, harvest tissue specimens, inject a medical fluid, and seal tissue openings. In the illustrated example, treatment instrument (300) comprises an end effector (310), a vacuum cannula (320), and a probe (330). In this version, end effector (310) is similar to end effector (110) described above and comprises a hollow, cylindrical body (312) having a longitudinal axis, a distal opening (314) and a plurality of cutting features (316). In the illustrated example, vacuum cannula (320) comprises a hollow, cylindrical body (322) having a distal opening (324). Cylindrical body (322) of vacuum cannula (320) may comprise one or more openings, such as in the example shown in FIGS. 16-17, although this is not required.

As shown, cylindrical body (322) of vacuum cannula (320) is positioned co-axially within end effector (310). In the illustrated example, probe (330) is positioned co-axially within vacuum cannula (320). As illustrated best in FIG. 8, treatment instrument (300) comprises a delivery channel (325) defined by the inner surface (313) of end effector (310) and the outer surface (323) of vacuum cannula (320). In the illustrated example, delivery channel (325) is in fluid communication with medical fluid reservoir (250) and/or saline reservoir (260) to provide distribution of a medical fluid and/or saline as described above. As shown, cutting features (316) comprise circular apertures in cylindrical body (322) that are in communication with delivery channel (325), such that the substance (e.g. medical fluid, saline, etc.) distributed through delivery channel (325) may be communicated through cutting features (316) to the target site. Cutting features (316) are also configured to debride a tissue surface when end effector (310) is rotated in a first direction and configured to harvest tissue specimens when end effector (310) is rotated in a second direction. End effector (310) may comprise any suitable number of cutting features (316) and cutting features (316) may be arranged in any configuration suitable to provide the desired functionality. Cutting features (316) may comprise a debriding surface that is sharpened or abrasive to remove tissue cells from the interior surface of fistula (430) during debriding; and a harvesting edge that is sharpened to slice through tissue surrounding the interior cavity of fistula (430) to obtain tissue specimens during harvesting. Cutting features (316) may be sized and shaped to harvest tissue specimens of a particular shape and/or particular dimensions. Cutting features (316) may comprise openings, sharp edges, projections, protuberances notches, or any other structure suitable to debride a tissue surface and/or harvest tissue specimens.

In addition, in the present example, interior surface (327) of vacuum cannula (320) defines a vacuum channel (328), which will be described in more detail below. The components of treatment instrument (300) may be configured to translate longitudinally and/or rotate in unison with one another. In some other versions, at least one of the components may be configured to translate longitudinally and/or rotate relative to at least one other component. By way of example only, end effector (310) may be configured to translate longitudinally and/or rotate relative to vacuum cannula (320) and/or probe (330). Other suitable arrangements of end effector (310), vacuum cannula (320), and probe (330) will be apparent to those of ordinary skill in the art based on the teachings herein.

Figure 9:
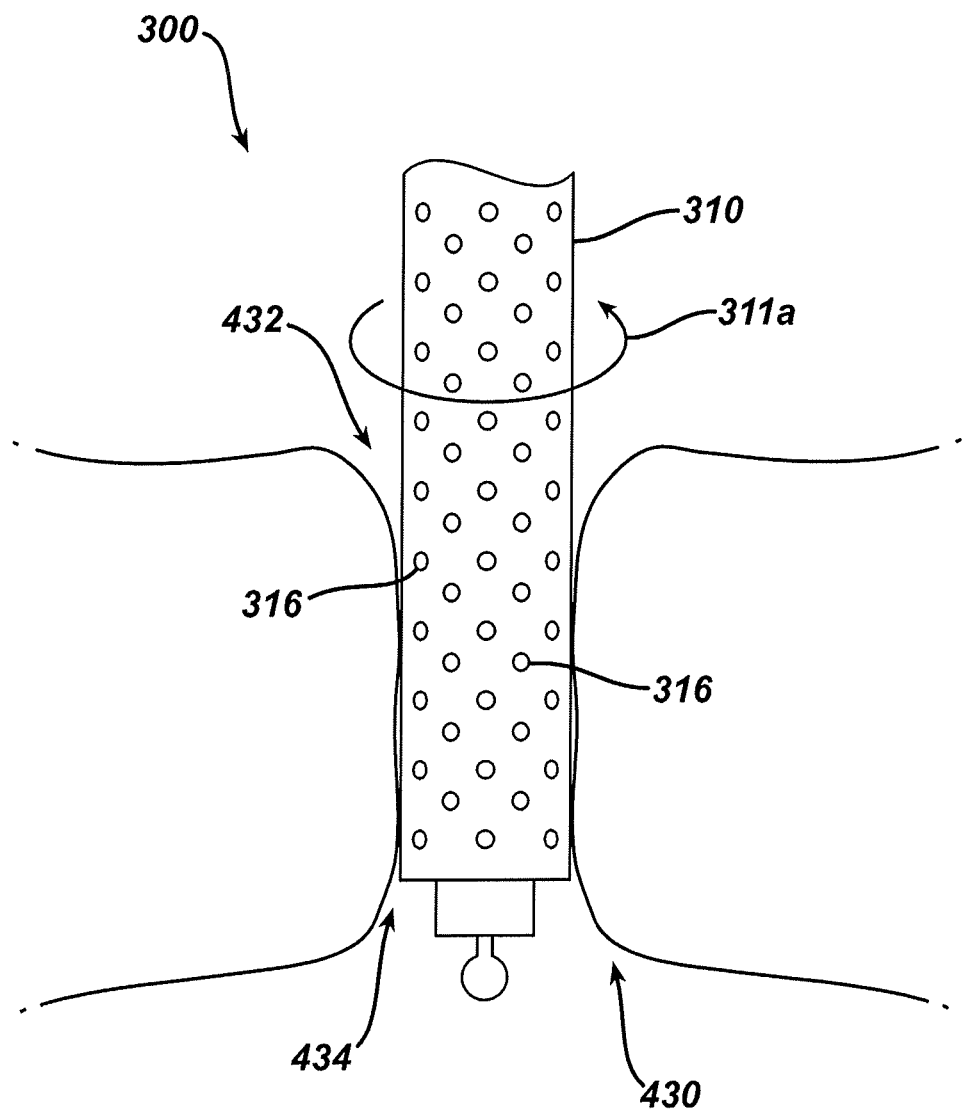
FIG. 9 depicts a front view of the instrument of FIG. 7 being used to debride a fistula.
Figure 10:
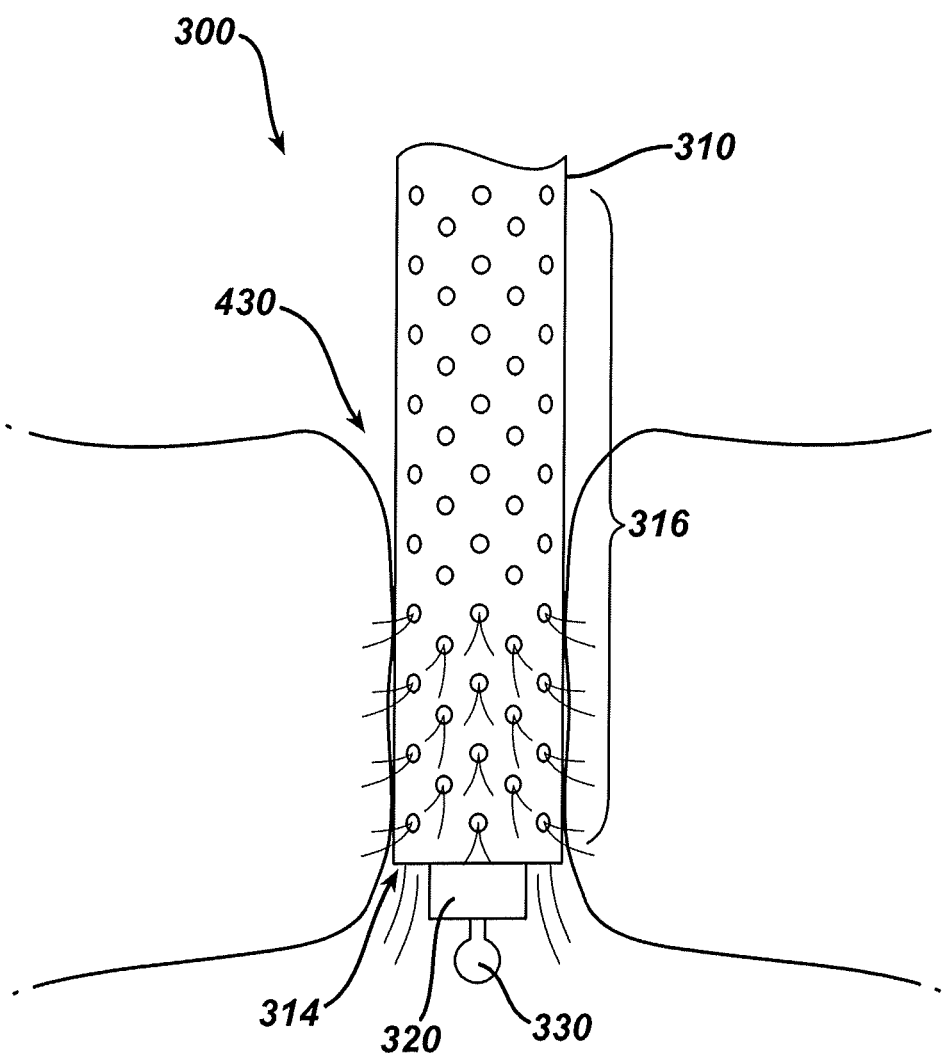
FIG. 10 depicts a front view of the instrument of FIG. 7 being flushed with saline to flush the fistula.

FIGS. 9-13 depict one merely illustrative example of treatment instrument (300) during various stages of treating a fistula. In particular, FIG. 9 depicts end effector (310) being used to debride the interior surface of a fistula (430). Debriding the interior of the fistula may remove epithelial cells from the interior surface of the fistula, which may facilitate healing and/or provide other results. Similar to end effector (110) and outer sheath (80) described above, treatment instrument (300) may be inserted directly into a patient such that at least a portion of end effector (310) reaches the target site (e.g. extends into the interior cavity of fistula (430)). Alternatively, similar to outer sheath (80) shown in FIG. 3, treatment instrument (300) may be inserted into a working channel of an endoscope and extended along the length of endoscope such that at least a portion of end effector (310) reaches the target site. The endoscope may provide additional channels to allow for the use of additional instruments, including but not limited to cameras and lights. The user may be able to extend and retract treatment instrument (300) within the patient and/or along the length of the endoscope. In some versions, the components of treatment instrument (300) may be extended and retracted in unison. Alternatively, the components of treatment instrument (300) may be extended and retracted independently of each other. This may be accomplished manually or with the aid of motorized or pneumatic extension means. In the present example, at least part of treatment instrument (300) reaches fistula (430) from an internal approach, such as via the patient's rectum. Of course, treatment instrument (300) may approach fistula (430) externally if desired (e.g., such that treatment instrument (300) is not inserted in the patient's rectum.

Similar to the method of treatment shown in FIGS. 2-5, in the method depicted in FIGS. 9-13 the target site is a fistula (430). Of course, instrument (300) may instead be used at any other suitable target site. As shown, during debriding (shown in FIG. 9), flushing (shown in FIG. 10), harvesting (shown in FIG. 11), and injection of the medical fluid (shown in FIG. 12), a distal portion of treatment instrument (300) is extended into the interior cavity of fistula (430). Treatment instrument (300) may be extended and retracted within fistula (430) manually by the user using any suitable mechanism. Alternatively, system (210) may comprise a motorized or pneumatic means for extending and retracting treatment instrument (300).

Figure 11:
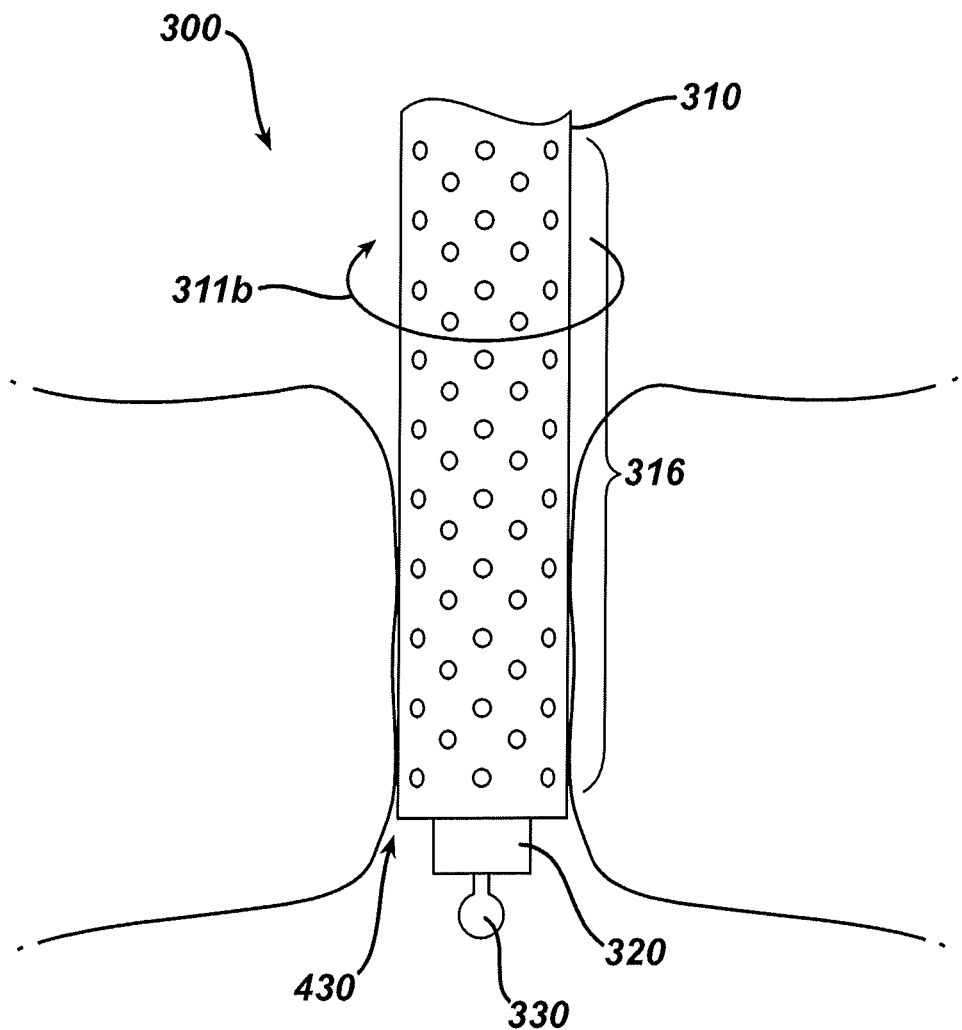
FIG. 11 depicts a front view of the instrument of FIG. 7 being used to obtain a tissue specimen from the fistula.

FIG. 9 depicts a debriding step in the illustrated treatment method. As shown, cutting features (316) are oriented such that debriding may be accomplished by rotating end effector (310) in a counter-clockwise direction, as indicated by arrow (311a) in FIG. 9. FIG. 11 depicts the harvesting step in the illustrated treatment method. As shown in FIG. 11, cutting features (316) are oriented such that harvesting may be accomplished by rotating end effector (310) in a clockwise direction, as indicated by arrow (311b) in FIG. 11. In the illustrated example, actuator (240) may be configured to selectively rotate end effector (310) in both counter-clockwise and clockwise directions. Of course, in some other versions, the orientation of cutting features (316) may be reversed such that debriding may be accomplished via clockwise rotation of end effector (310) and harvesting may be accomplished via counter-clockwise rotation of end effector (310). In still further versions, cutting features (316) may be configured and oriented such that both debriding and harvesting may be accomplished by rotating end effector (310) in a single direction, either counter-clockwise or clockwise, similar to the example shown in FIGS. 2-3 and described above.

Once the interior surface of fistula (430) has been adequately debrided, the loose pieces of debrided tissue may be flushed from delivery channel (325) of treatment instrument (300) and from the interior cavity of fistula (430) by delivering saline from saline reservoir (260) through delivery channel (325) into the interior cavity of fistula (430). As shown in FIG. 11, the saline may be distributed into the interior cavity of fistula (430) via distal opening (314) of end effector (310) and/or via the apertures defined by cutting features (316). Of course, the flushing step is optional and may be omitted in some versions or procedures. In some alternate versions, instead of flushing debrided tissue with saline or some other suitable substance, the debrided tissue may be removed from the target site using a vacuum communicated to the site through treatment instrument (300) or an auxiliary instrument. In some such versions, the vacuum may be initiated by vacuum source (230) or some other suitable vacuum source. It should also be understood that a combination of saline and vacuum may be used to remove debrided tissue.

After debridement and flushing (in some versions) then fistula (430) is ready for harvesting, which is shown in FIG. 11. A user may harvest tissue specimens from newly exposed tissue surrounding the interior cavity of fistula (430) by inserting at least a portion of end effector (310) into the interior cavity of fistula (430), or maintaining such a position if end effector (310) was already positioned there during debriding and/or flushing. Once end effector is positioned within fistula (430), tissue specimens may be harvested by rotating end effector (310) in a clockwise direction, as indicated by arrow 311b. As end effector (310) rotates, at least a portion of cutting features (316) will come into contact with tissue surrounding the interior cavity of fistula (430) and obtain one or more tissue specimens. Cutting features (316) may provide such cutting of tissue in a manner similar to that by which a manual cheese shredder shreds cheese. Debriding may remove a layer of epithelial cells from the interior surface of fistula (430), thereby exposing a layer of endothelial cells for harvesting. Harvesting tissue specimens comprising substantially endothelial cells, as opposed to specimens comprising substantially epithelial cells or a combination of the two types of cells, for use in the medical fluid may be desirable for some treatment methods, although it is not required.

During harvesting, cutting features (316) may come into contact with and slice through tissue surrounding the interior cavity of fistula (130), creating tissue specimens that are captured via openings in cutting features (116) and deposited into delivery channel (325) of treatment instrument (300). In some versions, the tissue specimens are communicated proximally toward medical fluid reservoir (250) using a vacuum initiated by vacuum source (230) and communicated through delivery channel (325) of treatment instrument (300). Vacuum cannula (320) may include transverse openings configured to allow tissue specimens to be received into vacuum channel (328) where the tissue specimens can then be communicated proximally via a vacuum initiated by vacuum source (230). In some such versions, vacuum channel (328) is in fluid communication with medical fluid reservoir (250).

Once the tissue specimens reach medical fluid reservoir (250), then the tissue specimens may be mixed with a substance contained within medical fluid reservoir (250). That substance may comprise a previously mixed medical fluid or a biocompatible material. By way of example only, the material mixed with harvested tissue specimens may provide a scaffold for the tissue specimens. It should also be understood that system (210) may include one or more features that are operable to dice, morcellate, and/or mince the harvested tissue specimens before and/or during mixing with a medical fluid and/or biocompatible material (e.g., scaffold material) in medical fluid reservoir (250). In still further versions, tissue specimens may remain contained within the interior lumen of end effector (210) as a substance is communicated distally from medical fluid reservoir (250). That substance may comprise a previously mixed medical fluid or a biocompatible material. Some other versions may incorporate other means for communicating tissue specimens proximally, including but not limited to a plunger, a vacuum initiated by a source other than vacuum source (30), or any other suitable device or method.

In still further versions, tissue specimens may remain contained within the distal portion of treatment instrument (300), such as within delivery channel (325), as a substance is communicated distally from medical fluid reservoir (250). That substance may comprise a previously mixed medical fluid or a biocompatible material. In some such versions, the tissue specimens may be mixed with the substance within treatment instrument (300) instead of within medical fluid reservoir (250). Still other suitable methods for mixing tissue specimens with biocompatible material and/or a pre-mixed medical fluid will be apparent to those of ordinary skill in the art based on the teachings herein.

Figure 12:
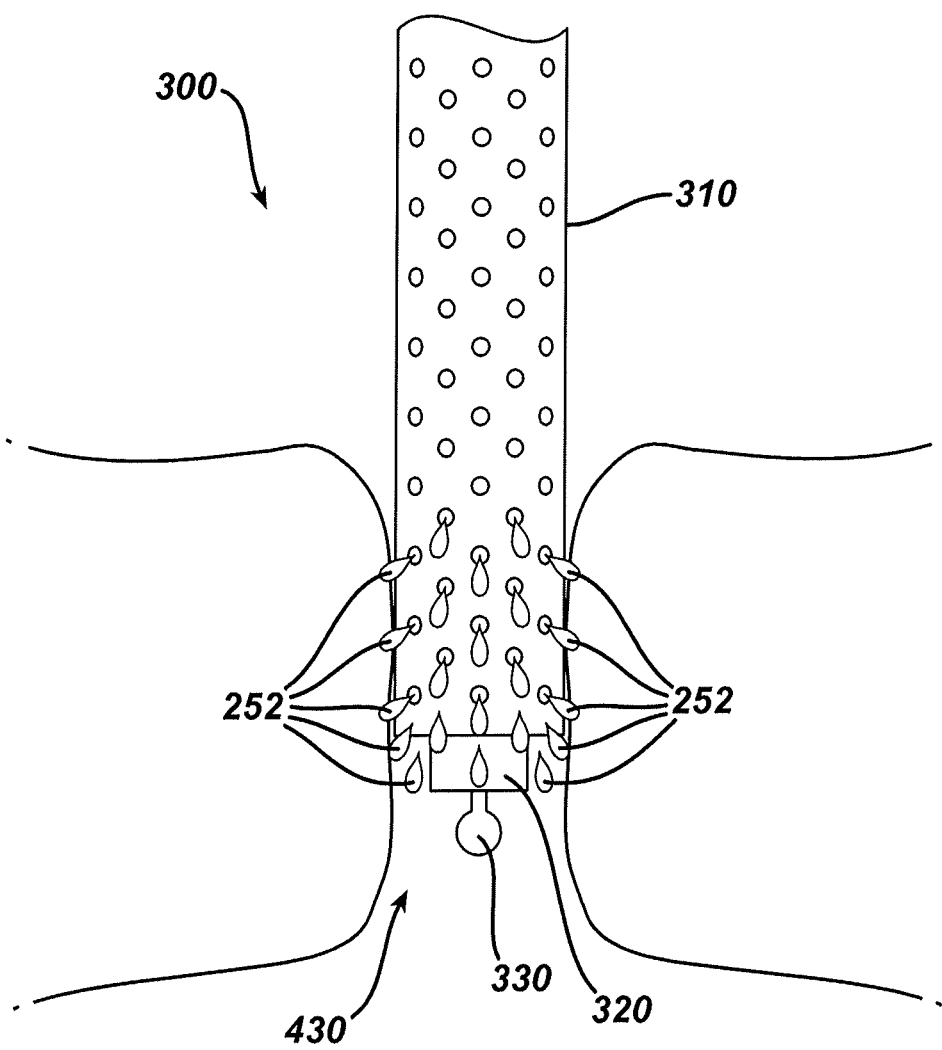
FIG. 12 depicts a front view of the instrument of FIG. 7 being used to administer a medical fluid in the fistula.

As shown in FIG. 12, a medical fluid (252) is distributed into the interior cavity of fistula (430). Specifically, in this version, medical fluid (52) is communicated through delivery channel (325) of treatment instrument (300) and into the fistula via cutting features (316). In some versions, medical fluid (52) may be distributed into fistula via distal opening (314) of end effector (310) in addition to or instead of being distributed via cutting features (316), but this is not required. Medical fluid (252) may be communicated from medical fluid reservoir (250) to treatment instrument (300) using any suitable device or method, including but not limited to tubing and conduits, a piston or pump mechanism, etc.

Treatment instrument (300) may be retracted proximally and at least partially removed from the interior cavity of fistula (430) once a sufficient amount of medical fluid (252) has been delivered. Medical fluid (252) may expand to fill the interior cavity of fistula (430) although this is not necessarily required. In some versions, end effector (310) may be retracted relative to the other components of treatment instrument (300) to expose distal portions of vacuum cannula (320) and probe (330). Alternatively, vacuum cannula (320) and/or probe (330) may be extended distally relative to end effector (310) to expose distal portions of vacuum cannula (320) and probe (330). In some versions, vacuum cannula (320) and probe (330) may be extended and retracted in unison, while, in some other versions, vacuum cannula (320) and probe (330) may be extended and retracted relative to each other to achieve the desired positioning of each component.

Figure 13:
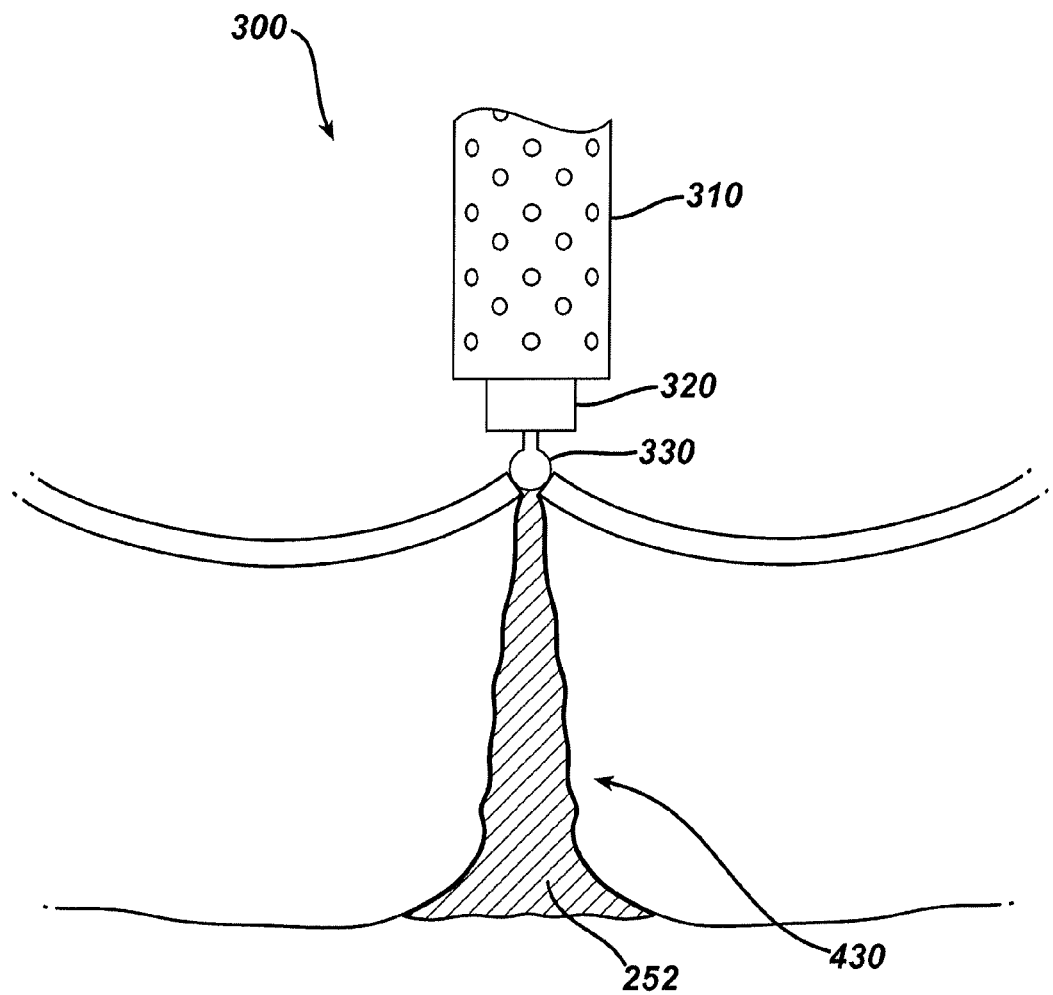
FIG. 13 depicts a front view of the instrument of FIG. 7 being used to seal a proximal end of the fistula.

As shown in FIG. 13, probe (330) is extended through distal opening (324) of vacuum cannula (320) so that probe (330) is adjacent to proximal opening (432) of fistula (430). Similar to probe (120) described above, probe (330) may comprise a monopolar RF device or a bipolar RF device. Control unit (220) may comprise suitable components required to provide the required energy via probe (330), including but not limited to circuit board(s), power source(s), and electrode(s). In some alternate versions, probe (120) may utilize a means for inducing coagulation of tissue other than RF energy. By way of example only, probe (330) may comprise a thermal heating device, a cryogenic device, an ultrasonic device, or any other suitable type of device. Various suitable ways in which probe (330) and associated components in control unit (210) may be configured will be apparent to those of ordinary skill in the art in view of the teachings herein.

In the treatment method depicted in FIG. 13, a vacuum is induced through vacuum cannula (320) as probe (330) and distal opening (324) of vacuum cannula (320) are positioned adjacent to proximal opening (432) of fistula (430). As shown, the vacuum draws the tissue surrounding proximal opening (432) together and toward probe (330) to facilitate coagulation of the tissue and sealing of proximal opening (432). The RF energy may be transmitted to the tissue as it comes into contact with probe (330). Once proximal opening (432) has been satisfactorily sealed, the user may remove treatment instrument (300) from the patient's rectum by retracting treatment instrument (300) proximally. In alternate treatment methods, probe (330) may be used to seal distal opening (434) of fistula (430) prior to injection of medical fluid (252). The sealing of distal opening (434) may occur at any point prior to injection of medical fluid (252) (e.g. prior to debriding, after debriding but prior to harvesting, etc.). Various other suitable ways in which system (210) may be used (in relation to a fistula (430) or otherwise) will be apparent to those of ordinary skill in the art in view of the teachings herein. Similarly, various ways in which components of system (210) may be provided, configured, and operable will be apparent to those of ordinary skill in the art in view of the teachings herein.

IV. Exemplary Alternative End Effectors

Figure 14:
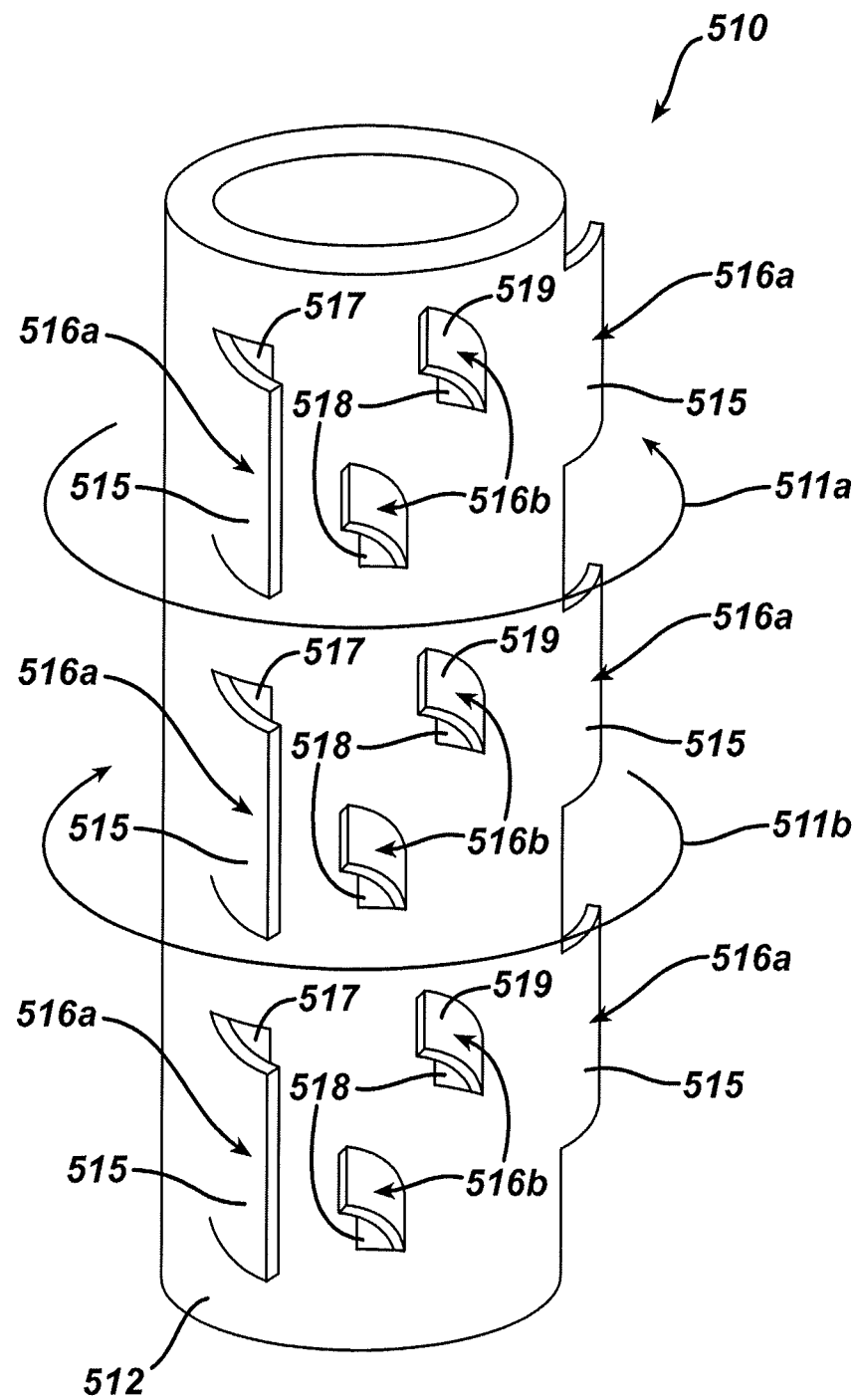
FIG. 14 depicts a perspective view of an exemplary alternative end effector.
Figure 15:
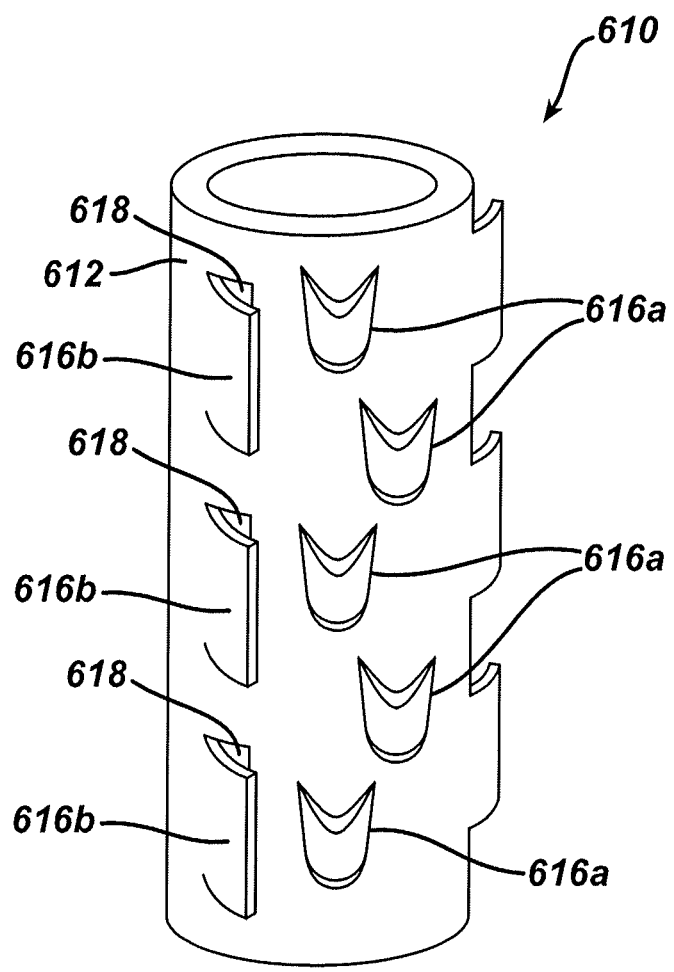
FIG. 15 depicts a perspective view of another exemplary alternative end effector.
Figure 16:
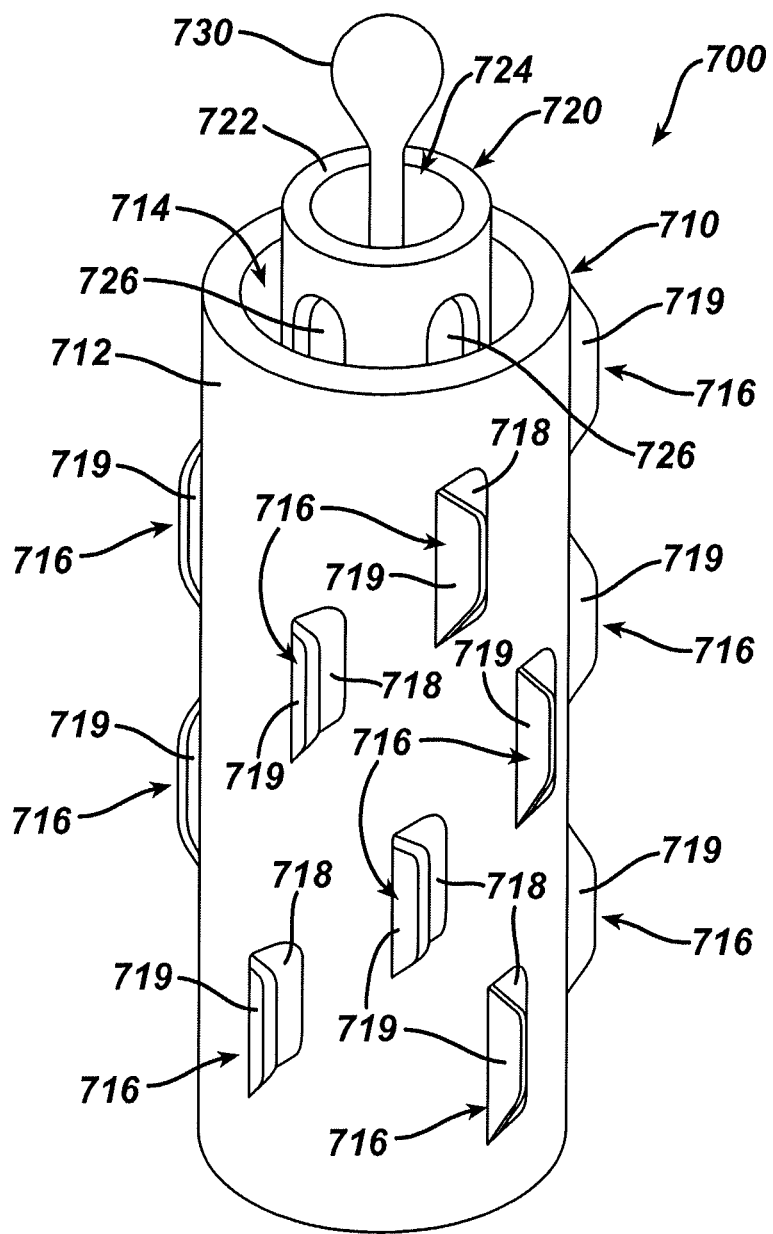
FIG. 16 depicts a perspective view of an exemplary alternative instrument.
Figure 17:
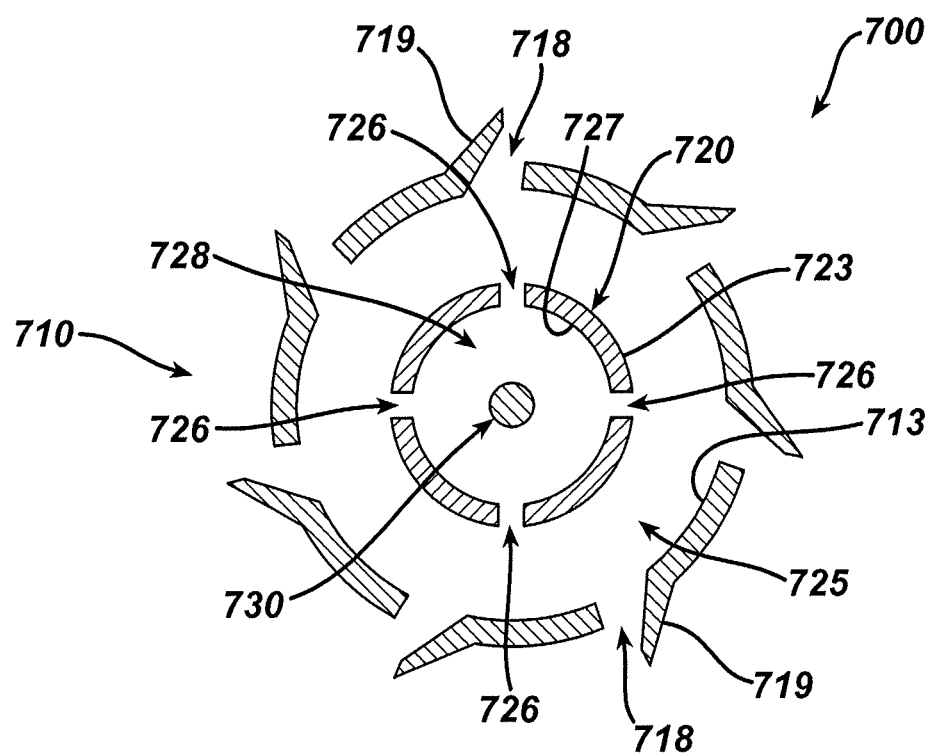
FIG. 17 depicts an end, cross-sectional view of the instrument of FIG. 16.
Figure 18:
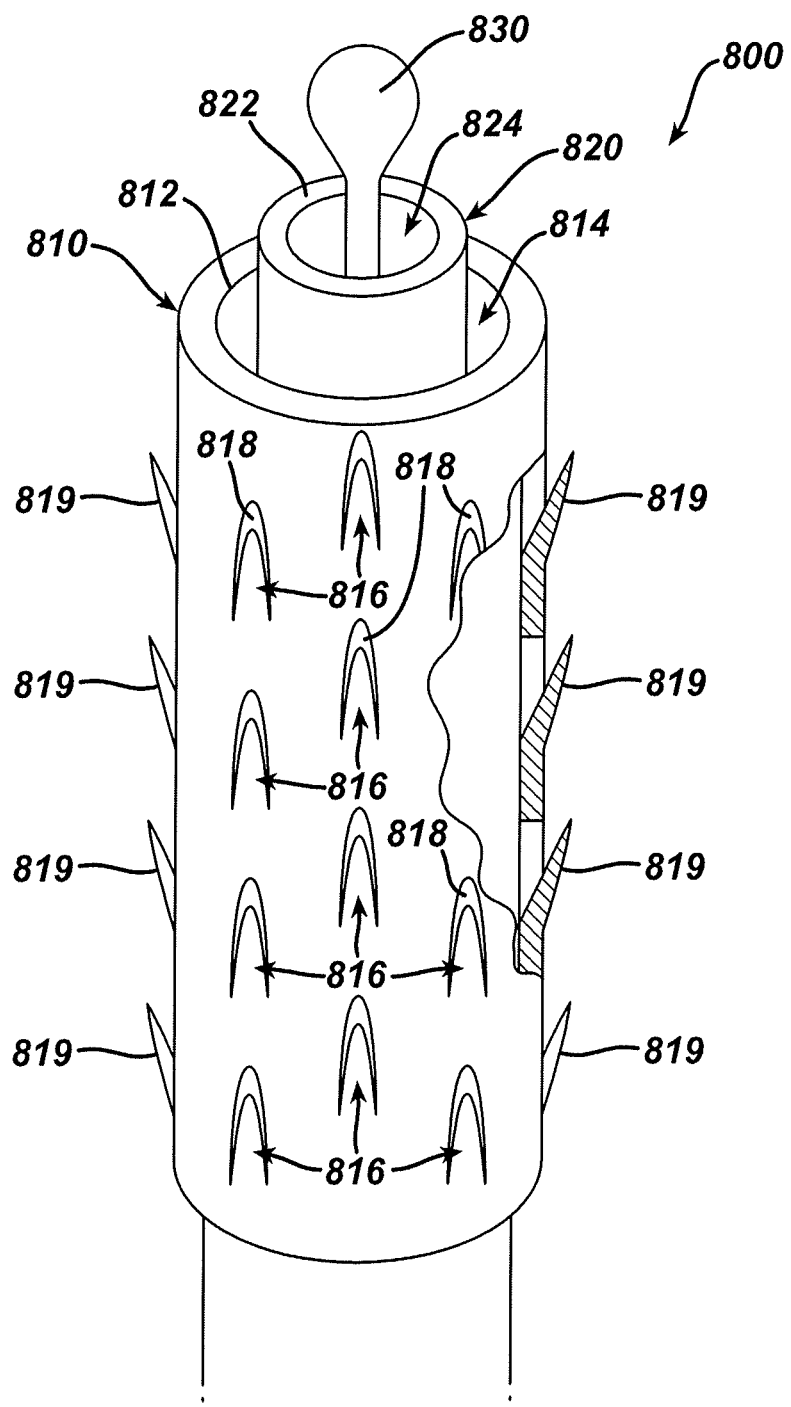
FIG. 18 depicts a perspective view of another exemplary alternative instrument.

FIGS. 14-15 depict alternate examples of end effectors that could be used with treatment system (10) and/or treatment system (210). FIGS. 16-18 depict alternate examples of treatment instruments that incorporate alternate end effectors (710, 810) that could also be used with treatment system (10) and/or treatment system (210). In particular, in treatment system (10), end effectors (510, 610, 710, 810) shown in FIGS. 14-18 could be used instead of end effector (110) shown in FIGS. 1-5. Similarly, in treatment system (210), end effectors (510, 610, 710, 810) could be used as part of treatment instrument (300) instead of end effector (310) shown in FIGS. 6-13. It will be appreciated that end effectors (110, 310, 510, 610, 710, 810) may be configured such that they are removable and replaceable. Accordingly, a user may change the particular end effector being used during a procedure without having to change other components of the treatment system. By way of example, a user may use a first end effector for debriding and a second end effector for harvesting. Of course, this is not required and a single end effector may be used for both debriding and harvesting.

As shown in FIG. 14, end effector (510) is configured to be used for both debriding and harvesting. Specifically, end effector (510) comprises a hollow, cylindrical body (512) and a plurality of cutting features (516a, 516b). In this version, the first set of cutting features (516a) is configured to debride a tissue surface, such as the interior surface of a fistula. As shown, cutting features (516a) are oriented such that a tissue surface may be debrided by rotating end effector (510) in a counter-clockwise direction, as indicated by arrow (511a). In this example, cutting features (516a) comprise curved projections (515) adjacent openings (517) in cylindrical body (512). Openings (517) may be in communication with the interior cavity of cylindrical body (512), such that debrided pieces of tissue may be collected within the interior cavity of cylindrical body (512). Openings (517) may allow for the communication of saline, a medical fluid (e.g., a cell/scaffold slurry, etc.), or some other suitable substance through cutting features (516a) as described above. Of course, in some versions, openings (517) may be omitted entirely. Cutting features (516a) may comprise openings, projections, protuberances, notches, or any other structure suitable to debride a tissue surface. In the present example, cutting features (516a) are formed by stamping a "U"-shaped cut in body (512), then folding the stamped portion back like a tab such that the cutting feature (516a) extends tangentially and/or outwardly from body (512), revealing a corresponding opening (517). Various other cutting features described herein may be formed in a similar fashion. Alternatively, any cutting feature described herein may be formed in any desired fashion.

In the illustrated example, the second set of cutting features (516b) are configured to harvest tissue specimens from tissue surrounding end effector (510), such as the tissue surrounding the interior cavity of a fistula. As shown, cutting features (516b) are oriented such that tissue specimens may be harvested by rotating end effector (510) in a clockwise direction, as indicated by arrow (511b). In this example, cutting features (516b) comprise curved projections (519) adjacent openings (518) in cylindrical body (512). In this example, curved projections (519) are longer than the curved projections (515) of cutting features (516a), although this is not necessarily required. Similar to openings (117, 517) described above, openings (518) may be in communication with the interior cavity of cylindrical body (512) such that tissue specimens may be collected within the interior cavity of cylindrical body (512) to be mixed with a pre-mixed medical fluid or biocompatible material. The curved projections (519) and openings (518) of cutting features (516b) may be sized and shaped to obtain tissue specimens of any desired size and shape. Cutting features (516b) may comprise openings, projections, protuberances, notches, or any other structure suitable to harvest tissue specimens. Cutting features (516b) may be formed in a manner similar to the method of forming cutting features (516a) described above. Alternatively, cutting features (516a, 516b) may be formed using any other suitable technique.

End effector (510) may comprise any suitable number of cutting features (516a, 516b) and cutting features (516a, 516b) may be arranged in any configuration suitable to provide the desired functionality. Of course, in some other versions, the orientation of cutting features (516a, 516b) may be reversed such that debriding may be accomplished via counter-clockwise rotation of end effector (510) and harvesting may be accomplished via clockwise rotation of end effector (510).

As shown in FIG. 15, end effector (610) is configured to be used for both debriding and harvesting. Specifically, end effector (610) comprises a hollow, cylindrical body (612) and a plurality of cutting features (616a, 616b). In this version, a first set of cutting features (616a) is configured to debride a tissue surface, such as the interior surface of a fistula. As shown, cutting features (616a) are triangular in shape and are oriented such that a tissue surface may be debrided by translating end effector (610) proximally and distally in a longitudinal direction. For instance, cutting features (616a) may debride epithelial cells from the wall of a fistula by rotating end effector (610) while extracting end effector (610) from the fistula. In this example, cutting features (616a) comprise oval-shaped projections on the exterior surface of cylindrical body (512). Cutting features (616a) may further comprise openings that are in communication with the interior cavity of cylindrical body (612), such that debrided pieces of tissue may be collected within the interior cavity of cylindrical body (612). Such openings may be defined by sharp edges and may allow for the communication of saline, a medical fluid, or some other suitable substance through cutting features (616a) as described above. In some versions, each cutting feature (616a) has one side opening that is larger than the other side opening in the direction trailing the rotational direction of end effector (610). Of course, in some versions, such openings may be omitted entirely or be otherwise configured. Cutting features (616a) may comprise openings, projections, protuberances, notches, or any other structure suitable to debride a tissue surface.

In the illustrated example, a second set of cutting features (616b) are configured to harvest tissue specimens from tissue surrounding end effector (610), such as the tissue surrounding the interior cavity of a fistula. As shown, cutting features (616b) are oriented such that tissue specimens may be harvested by rotating end effector (610) in a counter-clockwise direction. In this example, cutting features (616b) comprise curved projections (619) adjacent openings (618) in cylindrical body (612). Similar to openings (117, 517, 518) described above, openings (618) may be in communication with the interior cavity of cylindrical body (612) such that tissue specimens may be collected within the interior cavity of cylindrical body (612) to be mixed with a pre-mixed medical fluid or biocompatible material. The curved projections (619) and openings (618) of cutting features (616b) may be sized and shaped to obtain tissue specimens of any desired size and shape. Cutting features (616b) may comprise openings, projections, protuberances, notches, or any other structure suitable to harvest tissue specimens.

End effector (610) may comprise any suitable number of cutting features (616a, 616b), and cutting features (616a, 616b) may be arranged in any configuration suitable to provide the desired functionality. Of course, the orientation of cutting features (616a, 616b) may be altered such that debriding may be accomplished via counter-clockwise or clockwise rotation of end effector (610) and harvesting may be accomplished via proximal and distal translation of end effector (610).

V. Exemplary Multi-Functional Fistula Treatment Instruments

FIGS. 16-18 depict alternate examples of multi-functional treatment instruments that could be used with treatment system (210) to debride a tissue surface, harvest tissue specimens, inject a medical fluid, and seal tissue openings. In the example shown in FIGS. 16-17, treatment instrument (700) comprises end effector (710), vacuum cannula (720), and RF probe (730). In this version, end effector (710) is similar to end effectors (110, 310, 510, 610) described above and comprises a hollow, cylindrical body (712) having a longitudinal axis, a distal opening (714) and a plurality of cutting features (716). In the illustrated example, vacuum cannula (720) comprises a hollow, cylindrical body (722) having a distal opening (724). In this example, cylindrical body (722) of vacuum cannula (720) comprises a plurality of openings (726). As shown, cylindrical body (722) of vacuum cannula (720) is positioned co-axially within end effector (710). In the illustrated example, RF probe (730) is positioned co-axially within vacuum cannula (720). As illustrated best in FIG. 17, treatment instrument (700) comprises a delivery channel (725) defined by the inner surface (713) of end effector (710) and the outer surface (723) of vacuum cannula (720). Delivery channel (725) may be substantially similar to delivery channel (325) described above with regard to distribution of a medical fluid and/or saline.

In the illustrated example, end effector (710) comprises one type of cutting feature (716) that can be used both to debride a tissue surface and obtain tissue specimens when end effector (710) is rotated in a counter-clockwise direction. As shown, cutting features (716) comprise angled projections (719) extending from the outer surface of cylindrical body (712) that are adjacent openings (718) in cylindrical body (712). Similar to openings (117, 517, 518, 618) described above, openings (718) are in communication with the interior cavity or delivery channel (725) of cylindrical body (712) such that tissue specimens may be collected within the interior cavity of cylindrical body (712) to be mixed with a pre-mixed medical fluid or biocompatible material. Angled projections (719) and openings (718) of cutting features (716) may be sized and shaped to obtain tissue specimens of any desired size and shape. Cutting features (716) may comprise openings, projections, protuberances, notches, or any other structure suitable to harvest tissue specimens. In some other versions the orientation of cutting features (716) may be altered such that debriding and harvesting may be accomplished via clockwise rotation of end effector (710) and/or via longitudinal reciprocation of end effector (710). Of course, end effector (710) may comprise any suitable number of cutting features (716) and cutting features (716) may be arranged in any configuration suitable to provide the desired functionality.

In addition, in this example, interior surface (727) of vacuum cannula (720) defines a vacuum channel (728), which is similar to vacuum channel (328) described above. Vacuum cannula (720) further comprises openings (726) in cylindrical body (722). Openings (726) allow for fluid communication between delivery channel (725) and vacuum channel (728). In some versions, openings (726) may be used to communicate a vacuum into delivery channel (728) and through openings (718) in order to draw tissue into openings (718) for debriding and/or harvesting. Vacuum cannula (720) may comprise any suitable number of openings (726) and openings (726) may be arranged in any configuration suitable to provide the desired functionality. Of course, openings (726) in vacuum cannula (720) are merely optional and may be omitted entirely in some versions.

In the example shown in FIG. 18, treatment instrument (800) comprises end effector (810), vacuum cannula (820), and RF probe (830). In this version, end effector (810) is similar to end effectors (110, 310, 510, 610, 710) described above and comprises a hollow, cylindrical body (812) having a longitudinal axis, a distal opening (814) and a plurality of cutting features (816). In the illustrated example, vacuum cannula (820) comprises a hollow, cylindrical body (822) having a distal opening (824). In this example, cylindrical body (822) of vacuum cannula (820) is substantially solid, however, in some alternate versions cylindrical body (822) comprises one or more openings, similar to openings (726) described above. As shown, cylindrical body (822) of vacuum cannula (820) is positioned co-axially within end effector (810). In the illustrated example, RF probe (830) is positioned co-axially within vacuum cannula (820). Treatment instrument (800) may comprise a delivery channel defined by the inner surface of end effector (810) and the outer surface of vacuum cannula (820). A delivery channel in treatment instrument (810) may be substantially similar to delivery channels (325, 725) described above with regard to distribution of a medical fluid and/or saline, etc.

In the illustrated example, end effector (810) comprises one type of cutting feature (816) that can be used both to debride a tissue surface and obtain tissue specimens when end effector (810) is translated proximally and distally in a longitudinal direction. As shown, cutting features (816) comprise angled projections (819) extending from the outer surface of cylindrical body (812) that are adjacent openings (818) in cylindrical body (812). Similar to openings (117, 517, 518, 618, 718) described above, openings (818) may be in communication with the interior cavity of cylindrical body (812) such that tissue specimens may be collected within the interior cavity of cylindrical body (812) to be mixed with a pre-mixed medical fluid or biocompatible material. Angled projections (819) and openings (818) of cutting features (816) may be sized and shaped to obtain tissue specimens of any desired size and shape. Cutting features (816) may comprise openings, projections, protuberances, notches, or any other structure suitable to harvest tissue specimens. In some other versions, the orientation of cutting features (816) is altered such that debriding and harvesting may be accomplished via clockwise or counter-clockwise rotation of end effector (810). Of course, end effector (810) may comprise any suitable number of cutting features (816) and cutting features (816) may be arranged in any configuration suitable to provide the desired functionality.

VI. Exemplary Multi-Functional Fistula Treatment Instruments with Plungers

FIGS. 19-25 depict several different examples of multi-functional treatment instruments incorporating plungers that could be used with a treatment system, including but not limited to treatment systems (10, 210), to debride a tissue surface, harvest tissue specimens, and/or inject a medical fluid. Treatment instruments shown in FIGS. 19-25 may further be used in conjunction with a probe, such as probes (120, 330), to allow a user to seal a tissue opening. In the example shown in FIGS. 19-20, treatment instrument (1000) comprises end effector (1010) and plunger (1020). Again, treatment instrument (1000) may be configured for use with treatment systems (10, 210) described above, although this is not required. End effector (1010) may comprise a device substantially similar to one or more of end effectors (110, 310, 510, 610, 710, 810) described above, so the details of its construction will not be repeated here. Similar to end effectors (110, 310, 510, 610, 710, 810) described above, end effector (1010) may be used to debride, harvest tissue specimens, and/or deliver a medical fluid to a target site. As shown, the proximal end of end effector (1010) engages a connecting sheath (1030) that may couple end effector (1010) with a control unit (not shown). In the illustrated example, plunger (1020) comprises a distal head (1022) attached to a central shaft (1024). As shown, distal head (1022) is cone-shaped. Of course, distal head (1022) may comprise any suitable shape. Distal head (1022) may comprise a piercing tip configured to facilitate insertion of treatment instrument (1000) into and through tissue, although this is not required.

Figure 19:
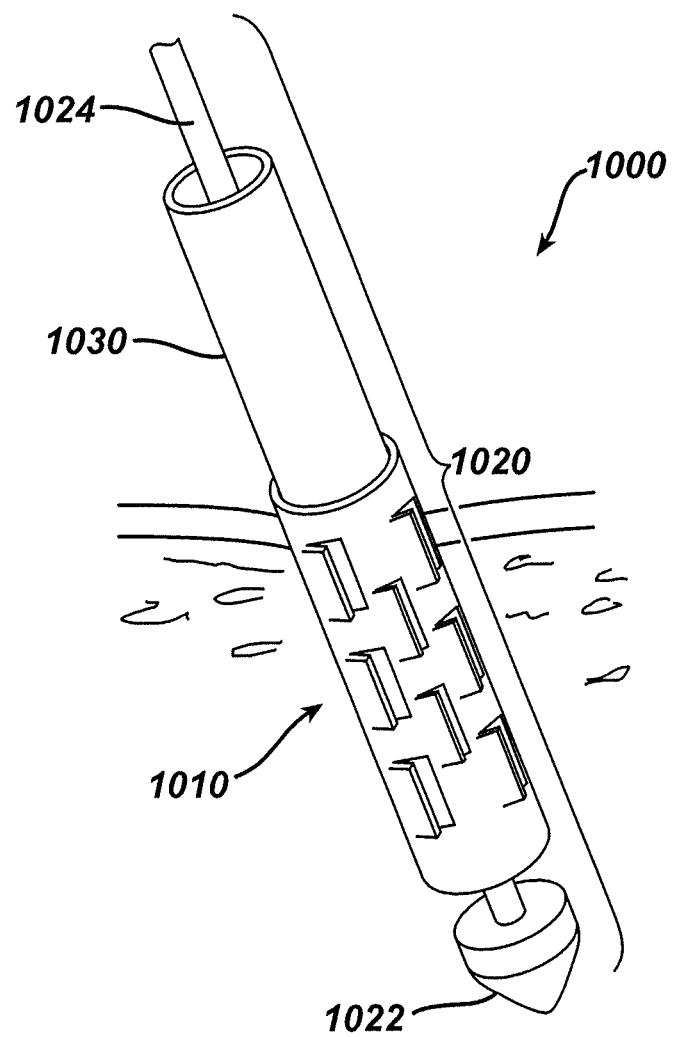
FIG. 19 depicts a perspective view of an exemplary alternative instrument comprising a plunger.
Figure 20:
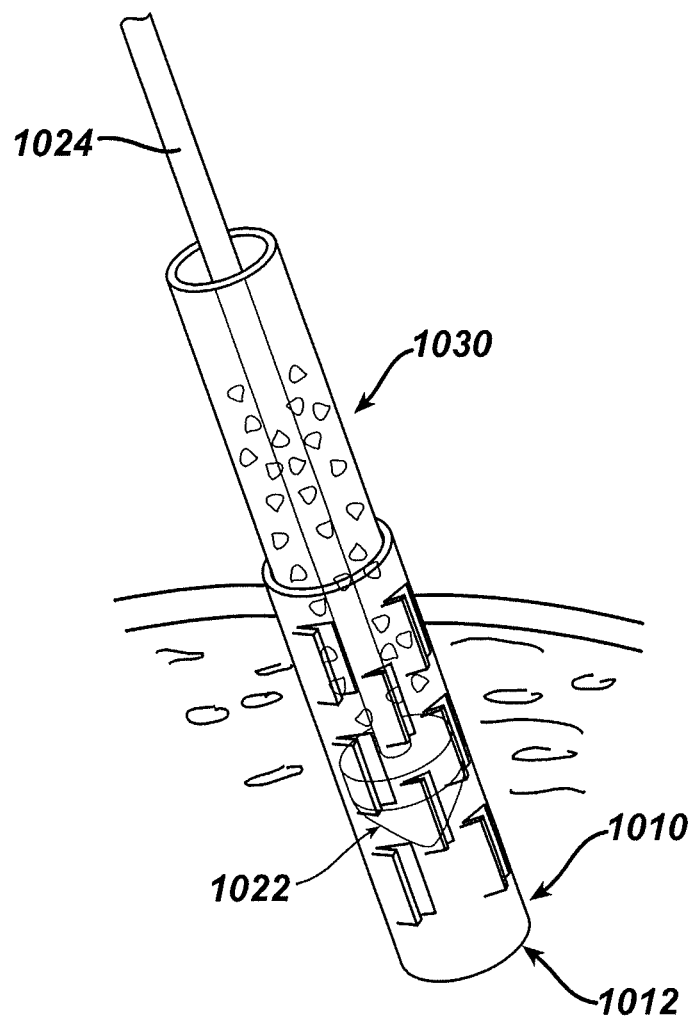
FIG. 20 depicts a perspective view of the instrument of FIG. 19 with the plunger being withdrawn.

As shown in FIGS. 19-20, plunger (1020) is positioned co-axially within the interior cavity of end effector (1010) and connecting sheath (1030). Plunger (1020) may be configured to translate longitudinally relative to end effector (1010). As shown in FIG. 19, distal head (1022) may be extended distally through the distal opening (1012) of end effector (1010). By way of example only, distal head (1022) may be extended through distal opening (1012) during flushing so that debrided tissue may be expelled from the interior cavity of end effector (1010) through distal opening (1012). In addition, distal head (1022) may be positioned such that distal head (1022) abuts distal opening (1012) during harvesting. Other suitable positions for distal head (1022) during various stages of treatment will be apparent to those of ordinary skill in the art based on the teachings herein. After the tissue specimens have been harvested and collected within the interior cavity of end effector (1010), plunger (1020) may be retracted to retrieve the tissue specimens as shown in FIG. 20. In this example, as plunger (1020) is retracted, distal head (1022) urges tissue specimens proximally through end effector (1010) and, subsequently, through connecting (1030). Retraction and extension of plunger (1020) may be accomplished manually or with the aid of motorized or pneumatic extension means, etc.

It should be noted that end effector (1010) and connecting (1030) are shown as being transparent in FIG. 20 to show plunger (1020). While end effector (1010) and connecting (1030) may be made from transparent material in some versions, end effector (1010) and connecting (1030) may comprise opaque or at least partially opaque material in some other versions. Of course, these components may have any other suitable properties or combination of properties.

Figure 21:
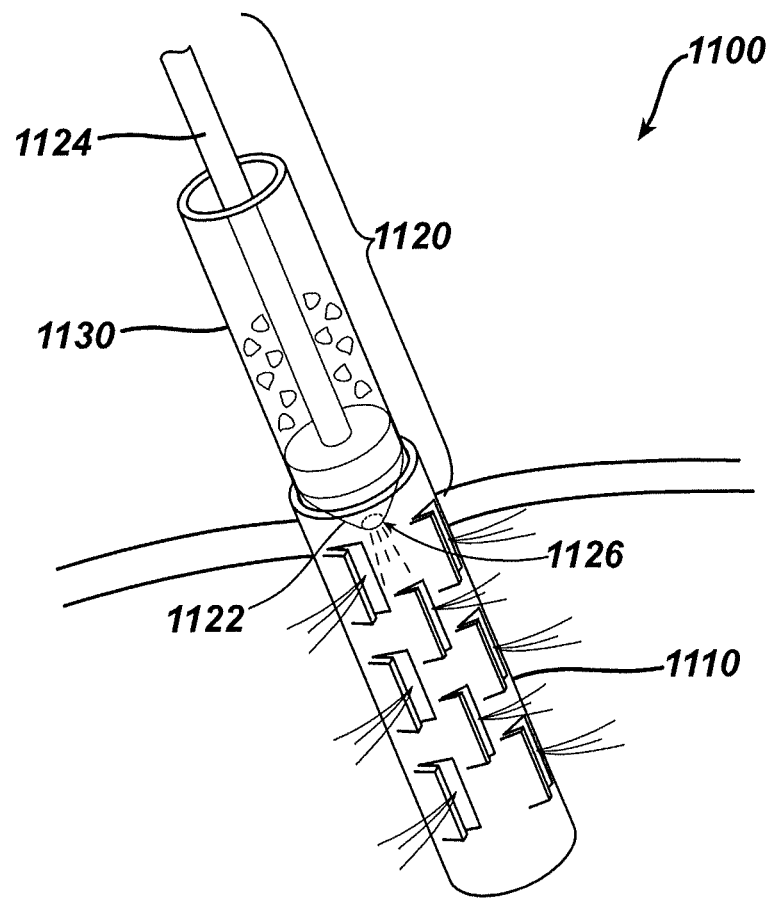
FIG. 21 depicts a perspective view of an instrument comprising an exemplary alternative plunger.

In the example shown in FIG. 21, treatment instrument (1100) comprises end effector (1110) and plunger (1120). Treatment instrument (1100) may be configured for use with treatment systems (10, 210) described above, although this is not required. End effector (1110) may comprise a device substantially similar to one or more of end effectors (110, 310, 510, 610, 710, 810, 1010) described above, so the details of its construction will not be repeated here. Similar to end effectors (110, 310, 510, 610, 710, 810, 1010) described above, end effector (1110) may be used to debride, harvest tissue specimens, and/or deliver a medical fluid to a target site. As shown, the proximal end of end effector (1110) engages a connecting sheath (1130) that may couple end effector (1110) with a control unit (not shown). In the illustrated example, plunger (1120) comprises a distal head (1122) attached to a central shaft (1124). As shown, distal head (1122) is cone-shaped. Of course, distal head (1122) may comprise any suitable shape. Distal head (1122) may comprise a piercing tip configured to facilitate insertion of treatment instrument (1100) into and through tissue, although this is not required.

As shown in FIG. 21, plunger (1120) is positioned co-axially within the interior cavity of end effector (1110) and connecting sheath (1130). Similar to plunger (1020) described above, plunger (1120) may be configured to translate longitudinally relative to end effector (1110). As a result, plunger (1120) may be used to retrieve tissue specimens after harvesting has been completed by retracting distal head (1122) proximally within end effector (1110) and connecting sheath (1130). In this example, central shaft (1124) is hollow, and distal head (1122) comprises a central opening (1126) aligned with the distal end of central shaft (1124). Central shaft (1124) may be in communication with a fluid or substance supply, such as medical fluid reservoir (50, 250) and/or saline reservoir (60, 260). Accordingly, any suitable substance, including but not limited to saline or a medical fluid, may be communicated distally through central shaft (1124) and into the interior cavity of end effector (1110) while plunger (1120) is still co-axially positioned within end effector (1110) or connecting sheath (1130). The substance may then be distributed to the surrounding area through one or more openings in end effector (1110), such as a distal opening and/or openings associated with cutting features, etc.

It should be noted that end effector (1110) and connecting (1130) are shown as being transparent in FIG. 21 to show plunger (1120). While end effector (1110) and connecting (1130) may be made from transparent material in some versions, end effector (1110) and connecting (1130) may comprise opaque or at least partially opaque material in some other versions. Of course, these components may have any other suitable properties or combination of properties.

In the example shown in FIG. 22, treatment instrument (1200) comprises end effector (1210) and plunger (1220). Treatment instrument (1200) may be configured for use with treatment systems (10, 210) described above, although this is not required. End effector (1210) may comprise a device substantially similar to one or more of end effectors (110, 310, 510, 610, 710, 810, 1010, 1110) described above, so the details of its construction will not be repeated here. Similar to end effectors (110, 310, 510, 610, 710, 810, 1010, 1110) described above, end effector (1210) may be used to debride, harvest tissue specimens, and/or deliver a medical fluid to a target site. As shown, the proximal end of end effector (1210) engages a connecting sheath (1230) that may couple end effector (1210) with a control unit (not shown). In the illustrated example, plunger (1220) comprises a distal head (1222) attached to a central shaft (1224). As shown, distal head (1122) is cone-shaped. Of course, distal head (1122) may comprise any suitable shape. Distal head (1222) may comprise a piercing tip configured to facilitate insertion of treatment instrument (1200) into and through tissue, although this is not required.

As shown in FIG. 22, plunger (1220) is positioned co-axially within the interior cavity of end effector (1210) and connecting sheath (1230). Similar to plungers (1020, 1120) described above, plunger (1220) may be configured to translate longitudinally relative to end effector (1210). As a result, plunger (1220) may be used to retrieve tissue specimens after harvesting has been completed by retracting distal head (1222) proximally within end effector (1210) and connecting sheath (1230). In this example, central shaft (1224) comprises a handle (1226) at a proximal end and an auger-like threading (1228) along a distal portion of central shaft (1224). As shown, a user may cause central shaft (1224) and threading (1228) to rotate by grasping and rotating handle (1226). In some other versions, central shaft (1224) may be rotated using any suitable means, including but not limited to motorized and pneumatic means. The rotation of threading (1228) may produce a cutting action to mince any previously collected tissue specimens that come into contact with threading (1228) during rotation. Mincing of the tissue specimens may be preferred for some methods of treatment, although this is not required. Threading (1228) may comprise a sharpened outer edge to facilitate the cutting action, although this is not required. Plunger (1220) may be configured to rotate in a single direction or multiple directions. Threading (1228) may be oriented such that it has either a right-hand or left-hand orientation. Of course, plunger (1220) may comprise any suitable length of threading (1228) and threading (1228) may be arranged in any configuration suitable to provide the desired functionality. It should also be understood that threading (1228) is merely one of many possible structures that may be provided to mince tissue specimens. Various other suitable structures that may be provided in addition to or in lieu of threading (1228) to mince tissue specimens will be apparent to those of ordinary skill in the art in view of the teachings herein.

Figure 23:
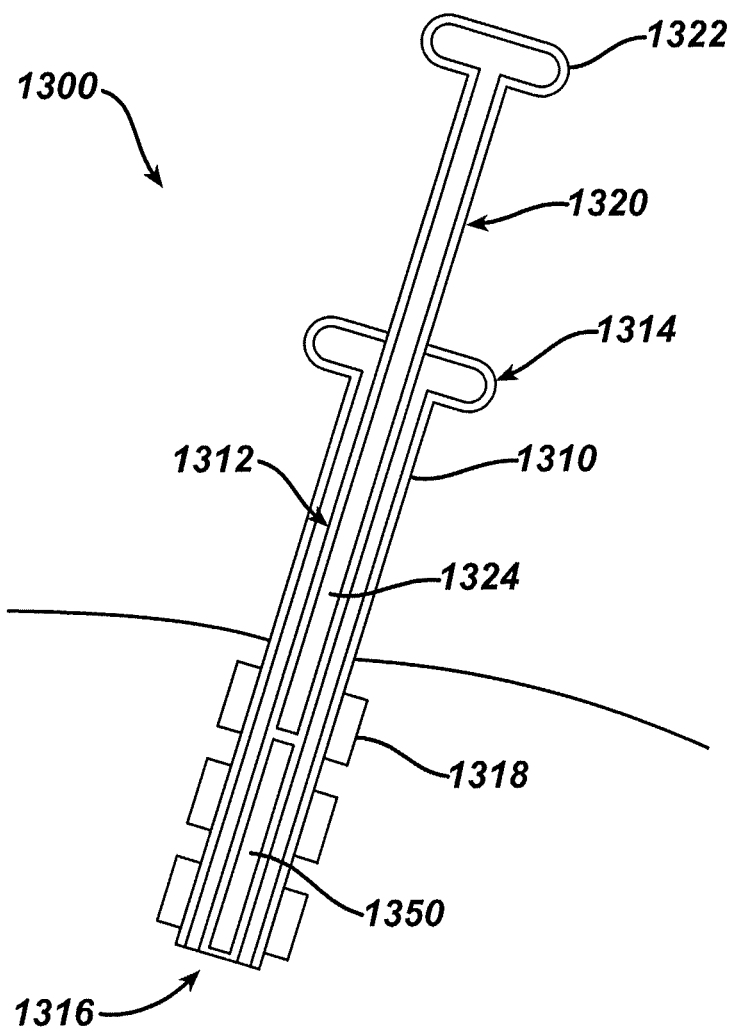
FIG. 23 depicts a cross-sectional, perspective view of an instrument comprising another exemplary alternative plunger, with a therapeutic plug in a pre-deployment position.
Figure 24:
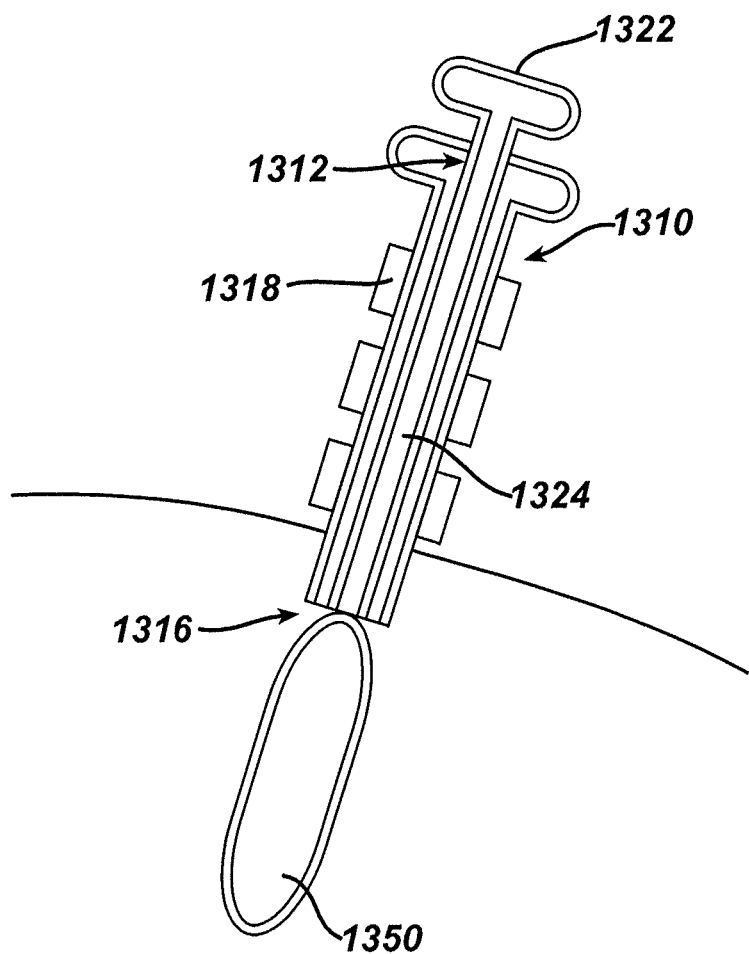
FIG. 24 depicts a cross-sectional, perspective view of the instrument of FIG. 23, with the therapeutic plug in a post-deployment position.
Figure 25:
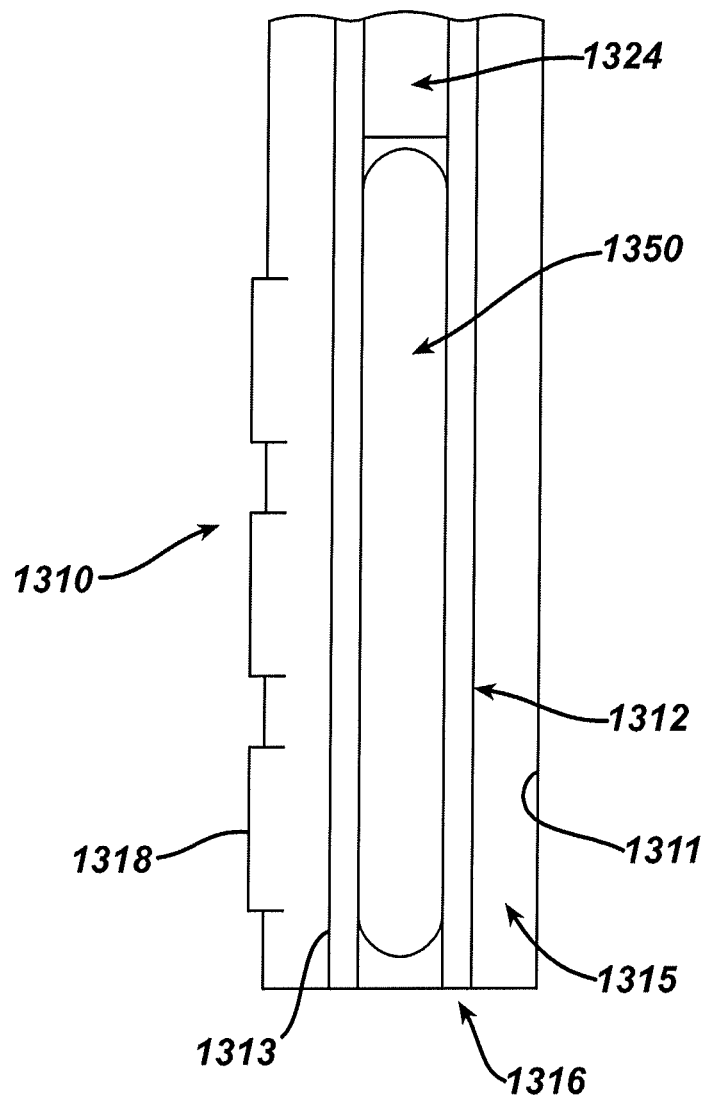
FIG. 25 depicts a front, cross-sectional view of the instrument of FIG. 23, with the therapeutic plug in a pre-deployment position.

In the example shown in FIGS. 23-25, treatment instrument (1300) comprises end effector (1310), plunger (1320), and a plug (1350). Treatment instrument (1300) may be configured for use with treatment systems (10, 210) described above, although this is not required. End effector (1210) may comprise a device substantially similar to one or more of end effectors (110, 310, 510, 610, 710, 810, 1010, 1110, 1210) described above, so the details of its construction will not be repeated here. Similar to end effectors (110, 310, 510, 610, 710, 810, 1010, 1110, 1210) described above, end effector (1310) may be used to debride, harvest tissue specimens, and/or deliver a medical fluid to a target site. For instance, end effector (1310) of the present example includes outwardly extending cutting/debriding members (1318). As shown, end effector (1310) includes an inner tube (1312) that extends along the entire length of end effector (1310). As best seen in FIG. 25, inner tube (1312) presents an outer surface (1313) that is radially spaced away from an inner surface (1311) that is presented by end effector (1310), such that a longitudinal channel (1315) is defined between surfaces (1311, 1313).

In this example, end effector (1310) further comprises a grasping portion (1314) attached to the proximal end of end effector (1310). Grasping portion (1314) may be configured to allow a user to grasp the proximal end of end effector (1310) while operating plunger (1320) with one hand In the illustrated example, plunger (1320) comprises a handle (1322) attached to the proximal end of a central shaft (1324). Central shaft (1324) is slidably positioned within inner tube (1312) of end effector (1310). The distal end of central shaft (1324) is adjacent to plug (1350), which is also positioned within inner tube (1312). Central shaft (1324) may be advanced and retracted along inner tube (1312) relative to end effector (1310) by pushing or pulling on handle (1322). Alternatively, central shaft (1324) may be advanced and retracted along inner tube (1312) relative to end effector by pushing or pulling on grasping portion (1314) of end effector (1310) while holding plunger (1320) stationary.

Plug (1350) is removably positioned within inner tube (1312). Plug (1350) may be urged distally along inner tube (1312) by central shaft (1324) as plunger (1320) is advanced distally within inner tube (1312) relative to end effector (1310). Plug (1350) may comprise collagen, polyglycolic acid, polylactic acid, polydioxanone, caprolactone, hemostatic sealants like oxidized regenerated cellulose, and/or any other substance or combination of substances suitable to absorb fluid and promote homeostasis at a target site. Plug (1350) may also be configured to expand upon deployment, although this is not necessarily required. Various other suitable materials that may be used to form plug (1350), as well as various other suitable properties of plug (1350), will be apparent to those of ordinary skill in the art in view of the teachings herein.

Plug (1350) may be loaded into inner tube (1312) of end effector (1310) prior to insertion of end effector (1310) into a patient. After plug (1350) is loaded, end effector (1310) may be inserted into a patient via any suitable method such that the distal opening (1316) of end effector (1310) is adjacent to a target site where the user desires to deploy plug (1350). Alternatively, plug (1350) may be loaded into inner tube (1312) of end effector (1310) after end effector (1310) has been inserted into a patient and distal opening (1316) has been positioned adjacent to a target site Once end effector (1310) has been is positioned for deployment, a user may deliver plug (1350) to the target site by holding plunger (1320) stationary while simultaneously retracting end effector (1310). Alternatively, a user may deliver plug (1350) to the target site by holding end effector (1310) stationary while simultaneously urging plunger (1320) distally within inner tube (1312). Other suitable methods of deploying plug (1350) using a combination of movement of plunger (1320) and end effector (1310) will be apparent to those of ordinary skill in the art based on the teachings herein. It should also be understood that end effector (1310) may be used to debride the target site, harvest tissue from the target site, and/or deliver a medical fluid to the target site before plug (1350) is deployed.

VII. Miscellaneous

While several devices and components thereof have been discussed in detail above, it should be understood that the components, features, configurations, and methods of using the devices discussed are not limited to the contexts provided above. In particular, components, features, configurations, and methods of use described in the context of one of the devices may be incorporated into any of the other devices. Furthermore, not limited to the further description provided below, additional and alternative suitable components, features, configurations, and methods of using the devices, as well as various ways in which the teachings herein may be combined and interchanged, will be apparent to those of ordinary skill in the art in view of the teachings herein.

Versions of the devices described above may be actuated mechanically or electromechanically (e.g., using one or more electrical motors, solenoids, etc.). However, other actuation modes may be suitable as well including but not limited to pneumatic and/or hydraulic actuation, etc. Various suitable ways in which such alternative forms of actuation may be provided in a device as described above will be apparent to those of ordinary skill in the art in view of the teachings herein.

Versions of the devices described above may have various types of construction. By way of example only, any of the devices described herein, or components thereof, may be constructed from suitable metals, ceramics, plastics, or combinations thereof. Furthermore, although not required, the construction of devices described herein may be configured to be compatible with or optimize their use with various imaging technologies. For instance, a device configured for use with MRI may be constructed from all non-ferromagnetic materials. Also for instance, when using optional imaging technologies with devices described herein, certain configurations may include modifications to materials of construction such that portions or the device may readily appear in a resultant image. Various suitable ways in which these and other modifications to the construction of devices described herein may be carried out will be apparent to those of ordinary skill in the art in view of the teachings herein.

Versions of the devices described above may have application in conventional medical treatments and procedures conducted by a medical professional, as well as application in robotic-assisted medical treatments and procedures.

Versions of described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A treatment instrument comprising:
   (a) an end effector, wherein the end effector defines a longitudinal axis, wherein the end effector comprises:
      (i) an exterior wall,
      (ii) a plurality of cutting features, wherein each cutting feature of the plurality of cutting features comprises a cutting edge and an adjacent aperture, wherein at least a portion of the plurality of cutting features are integrated into and extend outwardly from a portion of the exterior wall of the end effector, wherein at least a portion of the plurality of cutting features are configured to debride a tissue surface when the end effector is actuated, and
      (iii) an interior cavity; and
   (b) a plunger, wherein at least a portion of the plunger is translatable within the interior cavity of the end effector, wherein the plunger is separated from the outwardly extending cutting features by the exterior wall, wherein the plunger comprises:
      (i) a central shaft having a hollow interior, wherein the central shaft comprises a distal end, and
      (ii) a distal head, wherein the distal head is coupled with the distal end of the central shaft, wherein the distal head comprises a central opening on a distal end of the distal head, wherein the central opening is in communication with the hollow interior of the central shaft.

2. The treatment instrument of claim 1, wherein the distal head further comprises a cone-shaped tip.

3. The treatment instrument of claim 1, wherein the hollow interior of the central shaft is in fluid communication with at least one substance supply source, wherein the instrument is configured to communicate a substance distally from the supply source through the central shaft, through the central opening in the distal head and into the interior cavity of the end effector.

4. The treatment instrument of claim 3, wherein the substance is distributed to a target site through at least a portion of openings defined in the plurality of cutting features of the end effector.

5. The treatment instrument of claim 3, wherein the at least one substance supply source comprises at least one of a medical fluid reservoir or a saline reservoir.

6. The treatment instrument of claim 1 further comprising a connecting sheath coupled with a proximal end of the end effector.

7. The treatment instrument of claim 6, wherein at least a portion of the plunger is slidably positioned within the connecting sheath.

8. The treatment instrument of claim 1, wherein the plunger is manually translatable relative to the end effector.

9. The treatment instrument of claim 1, wherein the plunger further comprises a cutting feature operable to further cut tissue pieces severed by the end effector.

10. A treatment instrument comprising
    (a) an end effector, wherein the end effector comprises:
       a hollow, cylindrical body comprising an inner surface,
       (ii) an interior cavity defined by the inner surface of the cylindrical body, and
       (iii) a plurality of cutting features formed in the cylindrical body, wherein each cutting feature comprises an opening, wherein the plurality of cutting features are configured to debride a tissue surface when the end effector is actuated in a first rotational direction, wherein the plurality of cutting features are configured to harvest debrided tissue via each opening to collect tissue in the interior cavity of the end effector when the end effector is actuated in a second rotational direction, wherein the first direction is opposite to the second direction; and
    (b) a plunger positioned within the interior cavity of the end effector, wherein the plunger is configured to rotate and translate within the interior cavity of the end effector, wherein the plunger comprises:
       (i) a central shaft, wherein the central shaft comprises a cutting member, wherein the cutting member comprises a sharpened outer edge configured to mince the debrided tissue harvested by the cutting features, and
       (ii) a distal head, wherein the distal head is attached to a distal end of the central shaft such that the cutting member is located proximally to the distal head, wherein the distal head is configured to slidably engage the inner surface of the cylindrical body.

11. The treatment instrument of claim 10, wherein the central shaft further comprises a handle attached to a proximal end of the central shaft.

12. The treatment instrument of claim 10, wherein the plunger is configured to translate proximally and distally within the interior cavity of the end effector.

13. The treatment instrument of claim 10, wherein the cutting member comprises a threading extending from an exterior surface.

14. A treatment system comprising:
    (a) an end effector, wherein the end effector comprises
       (i) a distal opening,
       (ii) a plurality of cutting features along an outer surface of the end effector,
       (iii) an inner tube, wherein the inner tube extends substantially along the length of the end effector, and
       (iv) a longitudinal channel defined by the distal opening and an inner surface of the end effector, wherein the longitudinal channel extends along the length of the end effector, wherein the longitudinal channel is oriented coaxially about the inner tube;

(b) a plunger, wherein the plunger comprises a central shaft having a closed distal end, wherein the central shaft is slidably located within the inner tube of the end effector; and (c) a plug having a distal end, a proximal end, and a sidewall, wherein the distal end and the proximal end each define a solid face circumscribed by the sidewall, wherein the plug is slidably located within the inner tube of the end effector, wherein the plug is separate from and positioned distal to the distal end of the central shaft of the plunger, wherein the distal end of the central shaft is configured to engage the plug and urge the plug toward the distal opening of the end effector as the plunger translates distally relative to the end effector.

15. The treatment system of claim 14, wherein the plug comprises collagen.

16. The treatment system of claim 14, wherein the plug is configured to promote hemostasis at a target site upon exiting the end effector.

17. The treatment system of claim 14, wherein the plunger further comprises a handle attached to a proximal end of the central shaft.

18. The treatment system of claim 14, wherein the plug is configured to expand upon deployment from the distal opening of the end effector.

\* \* \* \* \*